(12) United States Patent
Pradeep et al.

(10) Patent No.: US 10,127,572 B2
(45) Date of Patent: Nov. 13, 2018

(54) STIMULUS PLACEMENT SYSTEM USING SUBJECT NEURO-RESPONSE MEASUREMENTS

(71) Applicants: Anantha Pradeep, Berkeley, CA (US); Robert T. Knight, Berkeley, CA (US); Ramachandran Gurumoorthy, Berkeley, CA (US)

(72) Inventors: Anantha Pradeep, Berkeley, CA (US); Robert T. Knight, Berkeley, CA (US); Ramachandran Gurumoorthy, Berkeley, CA (US)

(73) Assignee: The Nielsen Company, (US), LLC, New York, NY (US)

( * ) Notice: Subject to any disclaimer, the term of this patent is extended or adjusted under 35 U.S.C. 154(b) by 0 days.

(21) Appl. No.: 13/730,541

(22) Filed: Dec. 28, 2012

(65) Prior Publication Data

US 2013/0185141 A1    Jul. 18, 2013

Related U.S. Application Data

(63) Continuation of application No. 12/199,557, filed on Aug. 27, 2008, now Pat. No. 8,386,313.
(Continued)

(51) Int. Cl.
*G06Q 30/00* (2012.01)
*G06Q 30/02* (2012.01)
(Continued)

(52) U.S. Cl.
CPC ....... *G06Q 30/0242* (2013.01); *A61B 5/0402* (2013.01); *A61B 5/0482* (2013.01);
(Continued)

(58) Field of Classification Search
CPC ............... G06Q 10/0637; G06Q 30/02; G06Q 30/0242; G06Q 30/00; G06Q 30/0201;
(Continued)

(56) References Cited

U.S. PATENT DOCUMENTS

| 2,549,836 A | 4/1951 | McIntyre et al. |
| 3,490,439 A | 1/1970 | Rolston |

(Continued)

FOREIGN PATENT DOCUMENTS

| EP | 1087618 | 3/2001 |
| EP | 1609418 | 12/2005 |

(Continued)

OTHER PUBLICATIONS

Lachaux et al., "Measuring Phase Synchrony in Brain Signals," Human Brain Mapping 8 (1999), 194-208, 15 pages.
(Continued)

*Primary Examiner* — Scott S Trotter
(74) *Attorney, Agent, or Firm* — Hanley, Flight and Zimmerman, LLC

(57) ABSTRACT

Example methods, apparatus, systems and machine readable media are disclosed herein for selecting advertisement or entertainment location based on neuro-response data. An example method includes analyzing first neuro-response data from a first subject exposed to source material. The example method also includes identifying a candidate location in the source material for introduction of an advertisement or entertainment based on the first neuro-response data. In addition, the example method includes analyzing second neuro-response data from at least one of the first subject and a second subject exposed to a combination of the source material and the advertisement or entertainment inserted in the candidate location. The example also includes
(Continued)

determining an effectiveness of the advertisement or entertainment based on the second neuro-response data.

19 Claims, 8 Drawing Sheets

Related U.S. Application Data

(60) Provisional application No. 60/968,558, filed on Aug. 28, 2007.

(51) Int. Cl.
*A61B 5/0402* (2006.01)
*A61B 5/0482* (2006.01)
*A61B 5/0488* (2006.01)
*A61B 5/0496* (2006.01)
*A61B 5/00* (2006.01)

(52) U.S. Cl.
CPC .......... *A61B 5/0488* (2013.01); *A61B 5/0496* (2013.01); *A61B 5/4035* (2013.01)

(58) Field of Classification Search
CPC ........... G06Q 30/0244; G06Q 30/0269; G06Q 30/0271; A61B 5/0533; A61B 5/0402; A61B 5/04008; A61B 5/04012; A61B 5/0476; H04H 60/33; H04N 21/42201
USPC .......................................... 705/14.41, 14.66
See application file for complete search history.

(56) References Cited

U.S. PATENT DOCUMENTS

| | | |
|---|---|---|
| 3,572,322 A | 3/1971 | Wade |
| 3,735,753 A | 5/1973 | Pisarski |
| 3,880,144 A | 4/1975 | Coursin et al. |
| 3,901,215 A | 8/1975 | John |
| 3,998,213 A | 12/1976 | Price |
| 4,075,657 A | 2/1978 | Weinblatt |
| 4,145,122 A | 3/1979 | Rinard et al. |
| 4,149,716 A | 4/1979 | Scudder |
| 4,201,224 A | 5/1980 | John |
| 4,279,258 A | 7/1981 | John |
| 4,411,273 A | 10/1983 | John |
| 4,417,592 A | 11/1983 | John |
| 4,537,198 A | 8/1985 | Corbett |
| 4,557,270 A | 12/1985 | John |
| 4,610,259 A | 9/1986 | Cohen et al. |
| 4,613,951 A | 9/1986 | Chu |
| 4,626,904 A | 12/1986 | Lurie |
| 4,632,122 A | 12/1986 | Johansson et al. |
| 4,683,892 A | 8/1987 | Johansson et al. |
| 4,686,999 A | 8/1987 | Snyder et al. |
| 4,695,879 A | 9/1987 | Weinblatt |
| 4,736,751 A | 4/1988 | Gevins et al. |
| 4,800,888 A | 1/1989 | Itil et al. |
| 4,802,484 A | 2/1989 | Friedman et al. |
| 4,846,190 A | 7/1989 | John |
| 4,859,050 A | 8/1989 | Borah et al. |
| 4,870,579 A | 9/1989 | Hey |
| 4,885,687 A | 12/1989 | Carey |
| 4,894,777 A | 1/1990 | Negishi et al. |
| 4,913,160 A | 4/1990 | John |
| 4,967,038 A | 10/1990 | Gevins et al. |
| 4,955,388 A | 11/1990 | Silberstein |
| 4,973,149 A | 11/1990 | Hutchinson |
| 4,987,903 A | 1/1991 | Keppel et al. |
| 5,003,986 A | 4/1991 | Finitzo et al. |
| 5,010,891 A | 4/1991 | Chamoun |
| 5,038,782 A | 8/1991 | Gevins et al. |
| 5,052,401 A | 10/1991 | Sherwin |
| 5,083,571 A | 1/1992 | Prichep |
| RE34,015 E | 8/1992 | Duffy |
| 5,137,027 A | 8/1992 | Rosenfeld |
| 5,213,338 A | 5/1993 | Brotz |
| 5,226,177 A | 7/1993 | Nickerson |
| 5,243,517 A | 9/1993 | Schmidt et al. |
| 5,273,037 A | 12/1993 | Itil et al. |
| 5,291,888 A | 3/1994 | Tucker |
| 5,293,867 A | 3/1994 | Oommen |
| 5,295,491 A | 3/1994 | Gevins |
| 5,331,544 A | 7/1994 | Lu et al. |
| 5,339,826 A | 8/1994 | Schmidt et al. |
| 5,345,281 A | 9/1994 | Taboada et al. |
| 5,357,957 A | 10/1994 | Itil et al. |
| 5,363,858 A | 11/1994 | Farwell |
| 5,392,788 A | 2/1995 | Hudspeth |
| 5,406,956 A | 4/1995 | Farwell |
| 5,410,609 A | 4/1995 | Kado et al. |
| 5,436,830 A | 7/1995 | Zaltman |
| 5,447,166 A | 9/1995 | Gevins |
| 5,450,855 A | 9/1995 | Rosenfeld |
| 5,474,082 A | 12/1995 | Junker |
| 5,479,934 A | 1/1996 | Imran |
| 5,513,649 A | 5/1996 | Gevins et al. |
| 5,518,007 A | 5/1996 | Becker |
| 5,537,618 A | 7/1996 | Boulton et al. |
| 5,550,928 A | 8/1996 | Lu et al. |
| 5,617,855 A | 4/1997 | Waletzky et al. |
| 5,655,534 A | 8/1997 | Ilmoniemi |
| 5,676,138 A | 10/1997 | Zawilinski |
| 5,676,148 A | 10/1997 | Koo et al. |
| 5,687,322 A | 11/1997 | Deaton et al. |
| 5,720,619 A | 2/1998 | Fisslinger |
| 5,724,987 A | 3/1998 | Gevins et al. |
| 5,726,701 A | 3/1998 | Needham |
| 5,729,205 A | 3/1998 | Kwon |
| 5,736,986 A | 4/1998 | Sever, Jr. |
| 5,740,035 A | 4/1998 | Cohen et al. |
| 5,762,611 A | 6/1998 | Lewis et al. |
| 5,771,897 A | 6/1998 | Zufrin |
| 5,774,591 A | 6/1998 | Black et al. |
| 5,787,187 A | 7/1998 | Bouchard et al. |
| 5,800,351 A | 9/1998 | Mann |
| 5,802,208 A | 9/1998 | Podilchuk et al. |
| 5,802,220 A | 9/1998 | Black et al. |
| 5,812,642 A | 9/1998 | Leroy |
| 5,817,029 A | 10/1998 | Gevins et al. |
| 5,842,199 A | 11/1998 | Miller et al. |
| 5,848,399 A | 12/1998 | Burke |
| 5,892,566 A | 4/1999 | Bullwinkel |
| 5,945,863 A | 8/1999 | Coy |
| 5,961,332 A | 10/1999 | Joao |
| 5,974,262 A | 10/1999 | Fuller et al. |
| 5,983,129 A | 11/1999 | Cowan et al. |
| 5,995,868 A | 11/1999 | Dorfmeister et al. |
| 6,001,065 A | 12/1999 | DeVito |
| 6,016,475 A | 1/2000 | Miller et al. |
| 6,021,346 A | 2/2000 | Ryu et al. |
| 6,032,129 A | 2/2000 | Greef et al. |
| 6,052,619 A | 4/2000 | John |
| 6,088,040 A | 7/2000 | Oda et al. |
| 6,099,319 A | 8/2000 | Zaltman et al. |
| 6,120,440 A | 9/2000 | Goknar |
| 6,128,521 A | 10/2000 | Marro et al. |
| 6,154,669 A | 11/2000 | Hunter et al. |
| 6,155,927 A | 12/2000 | Levasseur et al. |
| 6,161,030 A | 12/2000 | Levendowski et al. |
| 6,170,018 B1 | 1/2001 | Voll et al. |
| 6,171,239 B1 | 1/2001 | Humphrey |
| 6,173,260 B1 | 1/2001 | Slaney |
| 6,175,753 B1 | 1/2001 | Menkes et al. |
| 6,182,113 B1 | 1/2001 | Narayanaswami |
| 6,190,314 B1 | 2/2001 | Ark et al. |
| 6,212,502 B1 | 4/2001 | Ball et al. |
| 6,228,038 B1 | 5/2001 | Claessens |
| 6,236,885 B1 | 5/2001 | Hunter et al. |
| 6,236,975 B1 | 5/2001 | Boe et al. |
| 6,254,536 B1 | 7/2001 | DeVito |
| 6,280,198 B1 | 8/2001 | Calhoun et al. |
| 6,286,005 B1 | 9/2001 | Cannon |
| 6,289,234 B1 | 9/2001 | Mueller |

(56) References Cited

U.S. PATENT DOCUMENTS

| | | |
|---|---|---|
| 6,292,688 B1 | 9/2001 | Patton |
| 6,299,308 B1 | 10/2001 | Voronka et al. |
| 6,301,493 B1 | 10/2001 | Marro et al. |
| 6,315,569 B1 | 11/2001 | Zaltman |
| 6,330,470 B1 | 12/2001 | Tucker et al. |
| 6,334,778 B1 | 1/2002 | Brown |
| 6,358,201 B1 | 3/2002 | Childre et al. |
| 6,370,513 B1 | 4/2002 | Kolawa et al. |
| 6,374,143 B1 | 4/2002 | Berrang et al. |
| 6,381,481 B1 | 4/2002 | Levendowski et al. |
| 6,398,643 B1 | 6/2002 | Knowles et al. |
| 6,422,999 B1 | 7/2002 | Hill |
| 6,434,419 B1 | 8/2002 | Gevins et al. |
| 6,435,878 B1 | 8/2002 | Reynolds et al. |
| 6,453,194 B1 | 9/2002 | Hill |
| 6,453,241 B1 | 9/2002 | Bassett, Jr. et al. |
| 6,487,444 B2 | 11/2002 | Mimura |
| 6,488,617 B1 | 12/2002 | Katz |
| 6,510,333 B1 | 1/2003 | Licata et al. |
| 6,510,340 B1 | 1/2003 | Jordan |
| 6,520,905 B1 | 2/2003 | Surve et al. |
| 6,545,685 B1 | 4/2003 | Dorbie |
| 6,575,902 B1 | 6/2003 | Burton |
| 6,577,329 B1 | 6/2003 | Flickner et al. |
| 6,585,521 B1 | 7/2003 | Obrador |
| 6,594,521 B2 | 7/2003 | Tucker |
| 6,598,006 B1 | 7/2003 | Honda et al. |
| 6,609,024 B1 | 8/2003 | Ryu et al. |
| 6,648,822 B2 | 11/2003 | Hamamoto et al. |
| 6,652,283 B1 | 11/2003 | Van Schaack et al. |
| 6,654,626 B2 | 11/2003 | Devlin et al. |
| 6,662,052 B1 | 12/2003 | Sarwal et al. |
| 6,665,560 B2 | 12/2003 | Becker et al. |
| 6,678,685 B2 | 1/2004 | McGill et al. |
| 6,688,890 B2 | 2/2004 | von Buegner |
| 6,708,051 B1 | 3/2004 | Durousseau |
| 6,712,468 B1 | 3/2004 | Edwards |
| 6,754,524 B2 | 6/2004 | Johnson, Jr. |
| 6,757,556 B2 | 6/2004 | Gopenathan et al. |
| 6,788,882 B1 | 9/2004 | Geer et al. |
| 6,792,304 B1 | 9/2004 | Silberstein |
| 6,842,877 B2 | 1/2005 | Robarts et al. |
| 6,850,252 B1 | 2/2005 | Hoffberg |
| 6,852,875 B2 | 2/2005 | Prakash |
| 6,888,457 B2 | 5/2005 | Wilkinson et al. |
| 6,904,408 B1 | 6/2005 | McCarthy et al. |
| 6,950,698 B2 | 9/2005 | Sarkela et al. |
| 6,958,710 B2 | 10/2005 | Zhang et al. |
| 6,973,342 B1 | 12/2005 | Swanson |
| 6,993,380 B1 | 1/2006 | Modarres |
| 7,020,508 B2 | 3/2006 | Stivoric et al. |
| 7,043,056 B2 | 5/2006 | Edwards et al. |
| 7,047,550 B1 | 5/2006 | Yasukawa et al. |
| 7,113,916 B1 | 9/2006 | Hill |
| 7,120,880 B1 | 10/2006 | Dryer et al. |
| 7,130,673 B2 | 10/2006 | Tolvanen-Laakso et al. |
| 7,150,715 B2 | 12/2006 | Collura et al. |
| 7,164,967 B2 | 1/2007 | Etienne-Cummings et al. |
| 7,177,675 B2 | 2/2007 | Suffin et al. |
| 7,222,071 B2 | 5/2007 | Neuhauser et al. |
| 7,246,081 B2 | 7/2007 | Hill |
| 7,249,708 B2 | 7/2007 | McConnell et al. |
| 7,272,982 B2 | 9/2007 | Neuhauser et al. |
| 7,286,871 B2 | 10/2007 | Cohen |
| 7,340,060 B2 | 3/2008 | Tomkins et al. |
| 7,359,894 B1 | 4/2008 | Liebman et al. |
| 7,391,835 B1 | 6/2008 | Gross et al. |
| 7,394,385 B2 | 7/2008 | Franco et al. |
| 7,408,460 B2 | 8/2008 | Crystal et al. |
| 7,420,464 B2 | 9/2008 | Fitzgerald et al. |
| 7,443,292 B2 | 10/2008 | Jensen et al. |
| 7,460,827 B2 | 12/2008 | Schuster et al. |
| 7,463,143 B2 | 12/2008 | Forr et al. |
| 7,463,144 B2 | 12/2008 | Crystal et al. |
| 7,471,987 B2 | 12/2008 | Crystal et al. |
| 7,483,835 B2 | 1/2009 | Neuhauser et al. |
| 7,483,844 B2 | 1/2009 | Takakura et al. |
| 7,496,400 B2 | 2/2009 | Hoskonen et al. |
| 7,548,774 B2 | 6/2009 | Kurtz et al. |
| 7,551,952 B2 | 6/2009 | Gevins et al. |
| 7,592,908 B2 | 9/2009 | Zhang et al. |
| 7,614,066 B2 | 11/2009 | Urdang et al. |
| 7,623,823 B2 | 11/2009 | Zito et al. |
| 7,630,757 B2 | 12/2009 | Dorfmeister et al. |
| 7,636,456 B2 | 12/2009 | Collins et al. |
| 7,650,793 B2 | 1/2010 | Jensen et al. |
| 7,658,327 B2 | 2/2010 | Tuchman et al. |
| 7,689,272 B2 | 3/2010 | Farwell |
| 7,697,979 B2 | 4/2010 | Martinerie et al. |
| 7,698,238 B2 | 4/2010 | Barletta et al. |
| 7,720,351 B2 | 5/2010 | Levitan |
| 7,729,755 B2 | 5/2010 | Laken |
| 7,765,564 B2 | 7/2010 | Deng |
| 7,774,052 B2 | 8/2010 | Burton et al. |
| 7,797,186 B2 | 9/2010 | Dybus |
| 7,809,420 B2 | 10/2010 | Hannula et al. |
| 7,840,248 B2 | 11/2010 | Fuchs et al. |
| 7,840,250 B2 | 11/2010 | Tucker |
| 7,844,484 B2 | 11/2010 | Arnett et al. |
| 7,865,394 B1 | 1/2011 | Calloway |
| 7,892,764 B2 | 2/2011 | Xiong et al. |
| 7,895,075 B2 | 2/2011 | Gettys et al. |
| 7,895,625 B1 | 2/2011 | Bryan et al. |
| 7,908,133 B2 | 3/2011 | Neuhauser |
| 7,917,366 B1 | 3/2011 | Levanon et al. |
| 7,930,199 B1 | 4/2011 | Hill |
| 7,962,315 B2 | 6/2011 | Jensen et al. |
| 7,988,557 B2 | 8/2011 | Soderland |
| 8,014,847 B2 | 9/2011 | Shastri et al. |
| 8,027,518 B2 | 9/2011 | Baker et al. |
| 8,055,722 B2 | 11/2011 | Hille |
| 8,065,203 B1 | 11/2011 | Chien et al. |
| 8,069,125 B2 | 11/2011 | Jung et al. |
| 8,073,707 B2 | 12/2011 | Teller et al. |
| 8,082,215 B2 | 12/2011 | Jung et al. |
| 8,086,563 B2 | 12/2011 | Jung et al. |
| 8,098,152 B2 | 1/2012 | Zhang et al. |
| 8,099,315 B2 | 1/2012 | Amento et al. |
| 8,103,328 B2 | 1/2012 | Turner et al. |
| 8,126,220 B2 | 2/2012 | Greig |
| 8,135,606 B2 | 3/2012 | Dupree |
| 8,151,298 B2 | 4/2012 | Begeja et al. |
| 8,165,916 B2 | 4/2012 | Hoffberg et al. |
| 8,196,168 B1 | 6/2012 | Bryan et al. |
| 8,200,775 B2 | 6/2012 | Moore |
| 8,209,224 B2 | 6/2012 | Pradeep et al. |
| 8,229,469 B2 | 7/2012 | Zhang et al. |
| 8,235,725 B1 | 8/2012 | Hill |
| 8,255,267 B2 | 8/2012 | Breiter |
| 8,270,814 B2 | 9/2012 | Pradeep et al. |
| 8,296,172 B2 | 10/2012 | Marci et al. |
| 8,300,526 B2 | 10/2012 | Saito et al. |
| 8,335,715 B2 | 12/2012 | Pradeep et al. |
| 8,381,244 B2 | 2/2013 | King |
| 8,386,312 B2 | 2/2013 | Pradeep et al. |
| 8,392,250 B2 | 3/2013 | Pradeep et al. |
| 8,392,251 B2 | 3/2013 | Pradeep et al. |
| 8,392,253 B2 | 3/2013 | Pradeep et al. |
| 8,392,254 B2 | 3/2013 | Pradeep et al. |
| 8,392,255 B2 | 3/2013 | Pradeep et al. |
| 8,396,744 B2 | 3/2013 | Pradeep et al. |
| 8,473,345 B2 | 6/2013 | Pradeep et al. |
| 8,484,801 B2 | 7/2013 | Pradeep et al. |
| 8,494,610 B2 | 7/2013 | Pradeep et al. |
| 8,494,905 B2 | 7/2013 | Pradeep et al. |
| 8,533,042 B2 | 9/2013 | Pradeep et al. |
| 8,548,852 B2 | 10/2013 | Pradeep et al. |
| 8,561,095 B2 | 10/2013 | Dimitrova et al. |
| 8,635,105 B2 | 1/2014 | Pradeep et al. |
| 8,655,428 B2 | 2/2014 | Pradeep et al. |
| 8,655,437 B2 | 2/2014 | Pradeep et al. |
| 8,764,652 B2 | 7/2014 | Lee et al. |
| 8,788,372 B2 | 7/2014 | Kettner et al. |
| 8,793,715 B1 | 7/2014 | Weitzenfeld et al. |

(56) References Cited

U.S. PATENT DOCUMENTS

| | | |
|---|---|---|
| 9,336,535 B2 | 5/2016 | Pradeep et al. |
| 9,560,984 B2 | 2/2017 | Pradeep et al. |
| 9,886,981 B2 | 2/2018 | Pradeep et al. |
| 2001/0013009 A1 | 8/2001 | Greening et al. |
| 2001/0020236 A1 | 9/2001 | Cannon |
| 2001/0029468 A1 | 10/2001 | Yamaguchi et al. |
| 2001/0032140 A1 | 10/2001 | Hoffman |
| 2001/0056225 A1 | 12/2001 | DeVito |
| 2002/0053076 A1 | 5/2002 | Landesmann |
| 2002/0055857 A1 | 5/2002 | Mault |
| 2002/0056087 A1 | 5/2002 | Berezowski et al. |
| 2002/0056124 A1 | 5/2002 | Hay |
| 2002/0059577 A1 | 5/2002 | Lu et al. |
| 2002/0065826 A1 | 5/2002 | Bell et al. |
| 2002/0072952 A1 | 6/2002 | Hamzey et al. |
| 2002/0077534 A1 | 6/2002 | DuRousseau |
| 2002/0082902 A1 | 6/2002 | Ando et al. |
| 2002/0103429 A1 | 8/2002 | deCharms |
| 2002/0111796 A1 | 8/2002 | Nemoto |
| 2002/0116042 A1 | 8/2002 | Boling |
| 2002/0143627 A1 | 10/2002 | Barsade et al. |
| 2002/0155878 A1 | 10/2002 | Lert, Jr. et al. |
| 2002/0156842 A1 | 10/2002 | Signes et al. |
| 2002/0169665 A1 | 11/2002 | Hughes et al. |
| 2002/0188216 A1 | 12/2002 | Kayyali et al. |
| 2002/0188217 A1 | 12/2002 | Farwell |
| 2002/0193670 A1 | 12/2002 | Garfield et al. |
| 2003/0013981 A1 | 1/2003 | Gevins et al. |
| 2003/0036955 A1 | 2/2003 | Tanaka |
| 2003/0037333 A1 | 2/2003 | Ghashghai et al. |
| 2003/0044050 A1 | 3/2003 | Clark et al. |
| 2003/0059750 A1 | 3/2003 | Bindler et al. |
| 2003/0063222 A1 | 4/2003 | Creed et al. |
| 2003/0065524 A1 | 4/2003 | Giacchetti et al. |
| 2003/0073921 A1 | 4/2003 | Sohmer et al. |
| 2003/0081834 A1 | 5/2003 | Philomin et al. |
| 2003/0093792 A1 | 5/2003 | Labeeb et al. |
| 2003/0100998 A2 | 5/2003 | Brunner et al. |
| 2003/0104865 A1 | 6/2003 | Itkis et al. |
| 2003/0131351 A1 | 7/2003 | Shapira |
| 2003/0149344 A1 | 8/2003 | Nizan |
| 2003/0165270 A1 | 9/2003 | Endrikhovski et al. |
| 2003/0177488 A1 | 9/2003 | Smith et al. |
| 2003/0204412 A1 | 10/2003 | Brier |
| 2003/0208754 A1 | 11/2003 | Sridhar et al. |
| 2003/0233278 A1 | 12/2003 | Marshall |
| 2004/0001616 A1 | 1/2004 | Gutta et al. |
| 2004/0005143 A1 | 1/2004 | Tsuru et al. |
| 2004/0013398 A1 | 1/2004 | Miura et al. |
| 2004/0015608 A1 | 1/2004 | Ellis et al. |
| 2004/0055448 A1 | 3/2004 | Byon |
| 2004/0068431 A1 | 4/2004 | Smith et al. |
| 2004/0073129 A1 | 4/2004 | Caldwell et al. |
| 2004/0092809 A1 | 5/2004 | DeCharms |
| 2004/0098298 A1 | 5/2004 | Yin |
| 2004/0101212 A1 | 5/2004 | Fedorovskaya et al. |
| 2004/0133081 A1 | 7/2004 | Teller et al. |
| 2004/0187167 A1 | 9/2004 | Maguire et al. |
| 2004/0193068 A1 | 9/2004 | Burton et al. |
| 2004/0210159 A1 | 10/2004 | Kibar et al. |
| 2004/0219184 A1 | 11/2004 | Brown et al. |
| 2004/0220483 A1 | 11/2004 | Yeo et al. |
| 2004/0236623 A1 | 11/2004 | Gopalakrishnan |
| 2005/0010475 A1 | 1/2005 | Perkowski et al. |
| 2005/0041951 A1 | 2/2005 | Inoue et al. |
| 2005/0043646 A1 | 2/2005 | Viirre et al. |
| 2005/0060312 A1 | 3/2005 | Curtiss et al. |
| 2005/0062637 A1 | 3/2005 | El Zabadani et al. |
| 2005/0071462 A1 | 3/2005 | Bodin et al. |
| 2005/0071865 A1 | 3/2005 | Martins |
| 2005/0076359 A1 | 4/2005 | Pierson et al. |
| 2005/0079474 A1 | 4/2005 | Lowe |
| 2005/0097594 A1 | 5/2005 | O'Donnell et al. |
| 2005/0107716 A1 | 5/2005 | Eaton et al. |
| 2005/0113649 A1 | 5/2005 | Bergantino |
| 2005/0132401 A1 | 6/2005 | Boccon-Gibod et al. |
| 2005/0143629 A1 | 6/2005 | Farwell |
| 2005/0149964 A1 | 7/2005 | Thomas et al. |
| 2005/0154290 A1 | 7/2005 | Langleben |
| 2005/0165766 A1 | 7/2005 | Szabo |
| 2005/0177058 A1 | 8/2005 | Sobell |
| 2005/0197590 A1 | 9/2005 | Osorio et al. |
| 2005/0203798 A1 | 9/2005 | Jensen et al. |
| 2005/0216071 A1 | 9/2005 | Devlin et al. |
| 2005/0216243 A1 | 9/2005 | Graham et al. |
| 2005/0223237 A1 | 10/2005 | Barletta et al. |
| 2005/0227233 A1 | 10/2005 | Buxton et al. |
| 2005/0240956 A1 | 10/2005 | Smith et al. |
| 2005/0256905 A1 | 11/2005 | Gruhl et al. |
| 2005/0261980 A1 | 11/2005 | Hadi |
| 2005/0267798 A1 | 12/2005 | Panara |
| 2005/0272017 A1 | 12/2005 | Neuhauser et al. |
| 2005/0273017 A1 | 12/2005 | Gordon |
| 2005/0273802 A1 | 12/2005 | Crystal et al. |
| 2005/0288954 A1 | 12/2005 | McCarthy et al. |
| 2005/0289582 A1 | 12/2005 | Tavares et al. |
| 2006/0003732 A1 | 1/2006 | Neuhauser et al. |
| 2006/0009702 A1 | 1/2006 | Iwaki et al. |
| 2006/0010470 A1 | 1/2006 | Kurosaki |
| 2006/0035707 A1 | 2/2006 | Nguyen et al. |
| 2006/0041548 A1 | 2/2006 | Parsons et al. |
| 2006/0042483 A1 | 3/2006 | Work et al. |
| 2006/0053110 A1 | 3/2006 | McDonald et al. |
| 2006/0069663 A1 | 3/2006 | Adar et al. |
| 2006/0093998 A1 | 5/2006 | Vertegaal |
| 2006/0111044 A1 | 5/2006 | Keller |
| 2006/0111644 A1 | 5/2006 | Guttag et al. |
| 2006/0129458 A1 | 6/2006 | Maggio |
| 2006/0167376 A1 | 7/2006 | Viirre et al. |
| 2006/0168613 A1 | 7/2006 | Wood et al. |
| 2006/0168630 A1 | 7/2006 | Davies |
| 2006/0176289 A1 | 8/2006 | Horn |
| 2006/0190822 A1 | 8/2006 | Basson et al. |
| 2006/0218046 A1 | 9/2006 | Carfi et al. |
| 2006/0256133 A1 | 11/2006 | Rosenberg |
| 2006/0257834 A1 | 11/2006 | Lee et al. |
| 2006/0259360 A1 | 11/2006 | Flinn et al. |
| 2006/0259371 A1 | 11/2006 | Perrier et al. |
| 2006/0293921 A1 | 12/2006 | McCarthy et al. |
| 2007/0016096 A1 | 1/2007 | McNabb |
| 2007/0038516 A1 | 2/2007 | Apple et al. |
| 2007/0048707 A1 | 3/2007 | Caamano et al. |
| 2007/0050256 A1 | 3/2007 | Walker et al. |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066874 A1 | 3/2007 | Cook |
| 2007/0066915 A1 | 3/2007 | Frei et al. |
| 2007/0066916 A1 | 3/2007 | Lemos |
| 2007/0067007 A1 | 3/2007 | Schulman et al. |
| 2007/0067305 A1 | 3/2007 | Ives |
| 2007/0078700 A1 | 4/2007 | Lenzmann et al. |
| 2007/0078706 A1 | 4/2007 | Datta et al. |
| 2007/0079331 A1 | 4/2007 | Datta et al. |
| 2007/0101360 A1 | 5/2007 | Gutta et al. |
| 2007/0106170 A1 | 5/2007 | Dunseath, Jr. et al. |
| 2007/0112460 A1 | 5/2007 | Kiselik |
| 2007/0135727 A1 | 6/2007 | Virtanen et al. |
| 2007/0135728 A1 | 6/2007 | Snyder et al. |
| 2007/0136753 A1 | 6/2007 | Bovenschulte et al. |
| 2007/0150916 A1 | 6/2007 | Begole et al. |
| 2007/0209047 A1 | 9/2007 | Hallberg et al. |
| 2007/0214471 A1 | 9/2007 | Rosenberg |
| 2007/0225585 A1 | 9/2007 | Washbon et al. |
| 2007/0225674 A1 | 9/2007 | Molnar et al. |
| 2007/0226760 A1 | 9/2007 | Neuhauser et al. |
| 2007/0235716 A1 | 10/2007 | Delic et al. |
| 2007/0238945 A1 | 10/2007 | Delic et al. |
| 2007/0244977 A1 | 10/2007 | Atkins |
| 2007/0250846 A1 | 10/2007 | Swix et al. |
| 2007/0250901 A1 | 10/2007 | McIntire et al. |
| 2007/0265507 A1 | 11/2007 | de Lemos |
| 2007/0282566 A1 | 12/2007 | Whitlow et al. |
| 2007/0294132 A1 | 12/2007 | Zhang et al. |

(56) References Cited

U.S. PATENT DOCUMENTS

| | | |
|---|---|---|
| 2007/0294705 A1 | 12/2007 | Gopalakrishnan |
| 2007/0294706 A1 | 12/2007 | Neuhauser et al. |
| 2008/0001600 A1 | 1/2008 | deCharms |
| 2008/0004940 A1 | 1/2008 | Rolleston Phillips |
| 2008/0010110 A1 | 1/2008 | Neuhauser et al. |
| 2008/0024725 A1 | 1/2008 | Todd |
| 2008/0027345 A1 | 1/2008 | Kumada et al. |
| 2008/0040740 A1 | 2/2008 | Plotnick et al. |
| 2008/0059997 A1 | 3/2008 | Plotnick et al. |
| 2008/0065468 A1 | 3/2008 | Berg et al. |
| 2008/0065721 A1 | 3/2008 | Cragun |
| 2008/0081961 A1 | 4/2008 | Westbrook et al. |
| 2008/0082019 A1 | 4/2008 | Ludving et al. |
| 2008/0086356 A1 | 4/2008 | Glassman et al. |
| 2008/0091463 A1 | 4/2008 | Shakamuri |
| 2008/0091512 A1 | 4/2008 | Marci et al. |
| 2008/0097854 A1 | 4/2008 | Young |
| 2008/0109840 A1 | 5/2008 | Walter et al. |
| 2008/0125110 A1 | 5/2008 | Ritter |
| 2008/0133724 A1 | 6/2008 | Clark |
| 2008/0147448 A1 | 6/2008 | Tunick et al. |
| 2008/0147742 A1 | 6/2008 | Allen |
| 2008/0152300 A1 | 6/2008 | Knee et al. |
| 2008/0162182 A1 | 7/2008 | Cazares et al. |
| 2008/0177197 A1 | 7/2008 | Lee et al. |
| 2008/0195471 A1 | 8/2008 | Dube |
| 2008/0204273 A1 | 8/2008 | Crystal et al. |
| 2008/0208072 A1 | 8/2008 | Fadem et al. |
| 2008/0214902 A1 | 9/2008 | Lee et al. |
| 2008/0218472 A1 | 9/2008 | Breen et al. |
| 2008/0221400 A1 | 9/2008 | Lee et al. |
| 2008/0221472 A1 | 9/2008 | Lee et al. |
| 2008/0221969 A1 | 9/2008 | Lee et al. |
| 2008/0222670 A1 | 9/2008 | Lee et al. |
| 2008/0222671 A1 | 9/2008 | Lee et al. |
| 2008/0228077 A1 | 9/2008 | Wilk et al. |
| 2008/0249865 A1 | 10/2008 | Angell et al. |
| 2008/0255949 A1 | 10/2008 | Genco et al. |
| 2008/0295126 A1 | 11/2008 | Lee et al. |
| 2008/0306398 A1 | 12/2008 | Uchiyama et al. |
| 2009/0018996 A1 | 1/2009 | Hunt et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0024747 A1 | 1/2009 | Moses et al. |
| 2009/0025023 A1 | 1/2009 | Pradeep et al. |
| 2009/0025024 A1 | 1/2009 | Beser et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030762 A1 | 1/2009 | Lee et al. |
| 2009/0030780 A1 | 1/2009 | York et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0037575 A1 | 2/2009 | Crystal et al. |
| 2009/0060240 A1 | 3/2009 | Coughlan et al. |
| 2009/0062679 A1 | 3/2009 | Tan et al. |
| 2009/0062680 A1 | 3/2009 | Sandford |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0069652 A1 | 3/2009 | Lee et al. |
| 2009/0070798 A1 | 3/2009 | Lee et al. |
| 2009/0082643 A1 | 3/2009 | Pradeep et al. |
| 2009/0082689 A1 | 3/2009 | Guttag et al. |
| 2009/0083129 A1 | 3/2009 | Pradeep et al. |
| 2009/0088610 A1 | 4/2009 | Lee et al. |
| 2009/0089830 A1 | 4/2009 | Chandratillake et al. |
| 2009/0094286 A1 | 4/2009 | Lee et al. |
| 2009/0094627 A1 | 4/2009 | Lee et al. |
| 2009/0094628 A1 | 4/2009 | Lee et al. |
| 2009/0094629 A1 | 4/2009 | Lee et al. |
| 2009/0097689 A1 | 4/2009 | Prest et al. |
| 2009/0112077 A1 | 4/2009 | Nguyen et al. |
| 2009/0131764 A1 | 5/2009 | Lee et al. |
| 2009/0132441 A1 | 5/2009 | Muller et al. |
| 2009/0133047 A1 | 5/2009 | Lee et al. |
| 2009/0138356 A1 | 5/2009 | Pomplun |
| 2009/0150919 A1 | 6/2009 | Lee et al. |
| 2009/0153328 A1 | 6/2009 | Otani et al. |
| 2009/0158308 A1 | 6/2009 | Weitzenfeld et al. |
| 2009/0163777 A1 | 6/2009 | Jung |
| 2009/0195392 A1 | 8/2009 | Zalewski |
| 2009/0214060 A1 | 8/2009 | Chuang et al. |
| 2009/0221928 A1 | 9/2009 | Einav et al. |
| 2009/0248484 A1 | 10/2009 | Surendran et al. |
| 2009/0248496 A1 | 10/2009 | Hueter et al. |
| 2009/0253996 A1 | 10/2009 | Lee et al. |
| 2009/0259137 A1 | 10/2009 | Delic et al. |
| 2009/0259509 A1 | 10/2009 | Landvater |
| 2009/0271294 A1 | 10/2009 | Hadi |
| 2009/0292587 A1 | 11/2009 | Fitzgerald |
| 2009/0300672 A1 | 12/2009 | Van Gulik |
| 2009/0305006 A1 | 12/2009 | Steffen |
| 2009/0318773 A1 | 12/2009 | Jung et al. |
| 2009/0318826 A1 | 12/2009 | Green et al. |
| 2009/0327068 A1 | 12/2009 | Pradeep et al. |
| 2009/0328089 A1 | 12/2009 | Pradeep et al. |
| 2010/0004977 A1 | 1/2010 | Marci et al. |
| 2010/0022821 A1 | 1/2010 | Dubi et al. |
| 2010/0041962 A1 | 2/2010 | Causevic et al. |
| 2010/0060300 A1 | 3/2010 | Muller et al. |
| 2010/0094702 A1 | 4/2010 | Silberstein |
| 2010/0125219 A1 | 5/2010 | Harris et al. |
| 2010/0145176 A1 | 6/2010 | Himes |
| 2010/0145215 A1 | 6/2010 | Pradeep et al. |
| 2010/0145217 A1 | 6/2010 | Otto et al. |
| 2010/0180029 A1 | 7/2010 | Fourman |
| 2010/0183279 A1 | 7/2010 | Pradeep et al. |
| 2010/0186031 A1 | 7/2010 | Pradeep et al. |
| 2010/0186032 A1 | 7/2010 | Pradeep et al. |
| 2010/0198042 A1 | 8/2010 | Popescu et al. |
| 2010/0214318 A1 | 8/2010 | Pradeep et al. |
| 2010/0215289 A1 | 8/2010 | Pradeep et al. |
| 2010/0218208 A1 | 8/2010 | Holden |
| 2010/0228604 A1 | 9/2010 | Desai et al. |
| 2010/0249538 A1 | 9/2010 | Pradeep et al. |
| 2010/0249636 A1 | 9/2010 | Pradeep et al. |
| 2010/0250325 A1 | 9/2010 | Pradeep et al. |
| 2010/0250458 A1 | 9/2010 | Ho |
| 2010/0257052 A1 | 10/2010 | Zito et al. |
| 2010/0268540 A1 | 10/2010 | Arshi et al. |
| 2010/0268573 A1 | 10/2010 | Jain et al. |
| 2010/0269127 A1 | 10/2010 | Krug |
| 2010/0274152 A1 | 10/2010 | McPeck et al. |
| 2010/0274153 A1 | 10/2010 | Tucker et al. |
| 2010/0292998 A1 | 11/2010 | Bodlaender et al. |
| 2010/0306120 A1 | 12/2010 | Ciptawilangga |
| 2010/0317988 A1 | 12/2010 | Terada et al. |
| 2010/0325660 A1 | 12/2010 | Holden |
| 2010/0331661 A1 | 12/2010 | Nakagawa |
| 2011/0004089 A1 | 1/2011 | Chou |
| 2011/0015503 A1 | 1/2011 | Joffe et al. |
| 2011/0040202 A1 | 2/2011 | Luo et al. |
| 2011/0046473 A1 | 2/2011 | Pradeep et al. |
| 2011/0046502 A1 | 2/2011 | Pradeep et al. |
| 2011/0046503 A1 | 2/2011 | Pradeep et al. |
| 2011/0046504 A1 | 2/2011 | Pradeep et al. |
| 2011/0047121 A1 | 2/2011 | Pradeep et al. |
| 2011/0059422 A1 | 3/2011 | Masaoka |
| 2011/0085700 A1 | 4/2011 | Lee |
| 2011/0098593 A1 | 4/2011 | Low et al. |
| 2011/0105937 A1 | 5/2011 | Pradeep et al. |
| 2011/0106621 A1 | 5/2011 | Pradeep et al. |
| 2011/0106750 A1 | 5/2011 | Pradeep et al. |
| 2011/0119124 A1 | 5/2011 | Pradeep et al. |
| 2011/0119129 A1 | 5/2011 | Pradeep et al. |
| 2011/0131274 A1 | 6/2011 | Hille |
| 2011/0144519 A1 | 6/2011 | Causevic |
| 2011/0153391 A1 | 6/2011 | Tenbrock |
| 2011/0208515 A1 | 8/2011 | Neuhauser |

(56) References Cited

U.S. PATENT DOCUMENTS

| | | |
|---|---|---|
| 2011/0224569 A1 | 9/2011 | Isenhart et al. |
| 2011/0237923 A1 | 9/2011 | Picht et al. |
| 2011/0237971 A1 | 9/2011 | Pradeep et al. |
| 2011/0248729 A2 | 10/2011 | Mueller et al. |
| 2011/0257502 A1 | 10/2011 | Lee |
| 2011/0257937 A1 | 10/2011 | Lee |
| 2011/0270620 A1 | 11/2011 | Pradeep et al. |
| 2011/0276504 A1 | 11/2011 | Pradeep et al. |
| 2011/0282231 A1 | 11/2011 | Pradeep et al. |
| 2011/0282232 A1 | 11/2011 | Pradeep et al. |
| 2011/0282749 A1 | 11/2011 | Pradeep et al. |
| 2011/0298706 A1 | 12/2011 | Mann |
| 2011/0319975 A1 | 12/2011 | Ho et al. |
| 2012/0004899 A1 | 1/2012 | Arshi |
| 2012/0022391 A1 | 1/2012 | Leuthardt |
| 2012/0036004 A1 | 2/2012 | Pradeep et al. |
| 2012/0036005 A1 | 2/2012 | Pradeep et al. |
| 2012/0046993 A1 | 2/2012 | Hill |
| 2012/0054018 A1 | 3/2012 | Pradeep et al. |
| 2012/0072289 A1 | 3/2012 | Pradeep et al. |
| 2012/0108995 A1 | 5/2012 | Pradeep et al. |
| 2012/0114305 A1 | 5/2012 | Holden |
| 2012/0130800 A1 | 5/2012 | Pradeep et al. |
| 2012/0173701 A1 | 7/2012 | Tenbrock |
| 2012/0203363 A1 | 8/2012 | McKenna et al. |
| 2012/0203559 A1 | 8/2012 | McKenna et al. |
| 2012/0239407 A1 | 9/2012 | Jain et al. |
| 2012/0245978 A1 | 9/2012 | Crystal et al. |
| 2013/0024272 A1 | 1/2013 | Pradeep et al. |
| 2013/0046577 A1 | 2/2013 | Marci et al. |
| 2013/0124365 A1 | 5/2013 | Pradeep |
| 2013/0152506 A1 | 6/2013 | Pradeep |
| 2013/0166373 A1 | 6/2013 | Pradeep et al. |
| 2013/0185140 A1 | 7/2013 | Pradeep et al. |
| 2013/0185142 A1 | 7/2013 | Pradeep et al. |
| 2013/0185144 A1 | 7/2013 | Pradeep et al. |
| 2013/0185145 A1 | 7/2013 | Pradeep et al. |
| 2013/0304540 A1 | 11/2013 | Pradeep et al. |
| 2013/0332259 A1 | 12/2013 | Pradeep et al. |

FOREIGN PATENT DOCUMENTS

| | | |
|---|---|---|
| GB | 1374658 | 11/1974 |
| GB | 2221759 | 2/1990 |
| JP | 2001147944 | 5/2001 |
| JP | 2005-160805 | 12/2003 |
| JP | 2005051654 | 2/2005 |
| JP | 2006006355 | 1/2006 |
| JP | 2006-305334 | 3/2006 |
| JP | 2006227994 | 8/2006 |
| KR | 200422399 | 7/2006 |
| WO | 95-018565 | 7/1995 |
| WO | 1997-017774 | 5/1997 |
| WO | 1997-040745 | 11/1997 |
| WO | 1997-041673 | 11/1997 |
| WO | 02-100241 | 12/2002 |
| WO | 02-102238 | 12/2002 |
| WO | 2004-049225 | 6/2004 |
| WO | 2006009771 | 1/2006 |
| WO | 2008030831 | 3/2008 |
| WO | 2008055078 | 5/2008 |
| WO | 2008-064431 | 6/2008 |
| WO | 2008-077178 | 7/2008 |
| WO | 2008-109694 | 9/2008 |
| WO | 2008-109699 | 9/2008 |
| WO | 2008-121651 | 10/2008 |
| WO | 2008-137579 | 11/2008 |
| WO | 2008-137581 | 11/2008 |
| WO | 2008-141340 | 11/2008 |
| WO | 2008-154410 | 12/2008 |
| WO | 2009-018374 | 2/2009 |
| WO | 2009-052833 | 4/2009 |
| WO | 2011-055291 | 5/2011 |
| WO | 2011-056679 | 5/2011 |

OTHER PUBLICATIONS

Lee et al., "What is 'neuromarketing'? A discussion and agenda for future research," International Journal of Psychophysiology, vol. 63, pp. 199-204, Elsevier (2006), 6 pages.

Lekakos, "Personalized Advertising Services Through Hybrid Recommendation Methods: The Case of Digital Interactive Television," Department of Informatics, Cyprus University, (2004), 11 pages.

Lewis et al., "Market Researchers make Increasing use of Brain Imaging," ACNR, vol. 5, No. 3, pp. 36-37, (Jul./Aug. 2005), 2 pages.

Luck et al., "The speed of visual attention in schizophrenia: Electrophysiological and behavioral evidence," Schizophrenia Research, pp. 174-195, Elsevier B.V. www.sciencedirect.com, (2006), 22 pages.

Lui et al., "Marketing Strategies in Virtual Worlds," The Data Base for Advances in Information Systems, vol. 38, No. 4, pp. 77-80, (Nov. 2007), 4 pages.

Makeig et al., "Mining event-related brain dynamics," TRENDS in Cognitive Sciences, vol. 8, No. 5, (May 2004), www.sciencedirect.com, 7 pages.

Makeig et al., "Dynamic Brain Sources of Visual Evoked Responses," Science, vol. 295, www.sciencemag.org, (Jan. 25, 2002), 5 pages.

The Mathworks, Inc., "MATLAB Data Analysis: Version 7," p. 4-19 (2005), 3 pages.

Meriam-Webster Online Dictionary definition for "tangible," available at http://www.meriam-webster.com/dictionary/tangible, 1 page.

Meriam Webster Online Dictionary, Definition of Virtual Reality, available at http://www.meriam-webster.com/dictionary/virtual%20reality, 2 page.

Miltner et al., "Coherence of gamma-band EEG activity as a basis for associative learning," Nature, vol. 397, www.nature.com, (Feb. 4, 1999), 3 pages.

Mosby's Dictionary of Medicine, Nursing, & Health Professions, 2009, Mosby, Inc., Definition of Alpha Wave, 1 page.

Mosby's Dictionary of Medicine, Nursing, & Health Professions, 2009, Mosby, Inc., Definition of Beta Wave, 1 page.

Neurofocus—Neuroscientific Analysis for Audience Engagement, accessed on Jan. 8, 2010 at http://web.archive.org/web/20080621114525/www.neurofocus.com /BrandImage.htm, (2008), 2 pages.

Newell et al., "Categorical perception of familiar objects," Cognition, vol. 85, Issue 2, pp. 113-143 (Sep. 2002), 31 pages.

Nielsen, "Neuroinformatics in Functional Neuroimaging," Informatics and Mathematical Modeling, Technical University of Denmark, (Aug. 30, 2002), 241 pages.

Oberman et al., "EEG evidence for mirror neuron activity during the observation of human and robot actions Aug. 29, 2012 Toward an analysis of the human qualities of interactive robots," Neurocomputing 70 (2007) 2194-2203, 10 pages.

Osborne, "Embedded Watermarking for image Verification in Telemedicine," Thesis submitted for the degree of Doctor of Philosophy, Electrical and Electronic Engineering, University of Adelaide (2005), 219 pages.

Padgett et al., "Categorical Perception in Facial Emotion Classification," In Proceedings of the 18th Annual Conference of the Cognitive Science Society, pp. 249-253 (1996), 5 pages.

Page et al., "Cognitive Neuroscience, Marketing and Research," Congress 2006—Foresight—The Predictive Power of Research Conference Papers, ESOMAR Publications, (Sep. 17, 2006), 25 pages.

Paller et al., "Validating neural correlates of familiarity," TRENDS in Cognitive Sciences, vol. 11, No. 6, www.sciencedirect.com, (May 2, 2007), 8 pages.

Palva et al., "Phase Synchrony Among Neuronal Oscillations in the Human Cortex," Journal of Neuroscience 25 (2005), 3962-3972, 11 pages.

Picton et al., "Guidelines for using human event-related potentials to study cognition: Recording standards and publication criteria," Psychophysiology, pp. 127-152, Society for Psychophysiological Research, (2000), 26 pages.

Rizzolatti et al., "The Mirror-Neuron System," Annu. Rev. Neurosci., vol. 27, pp. 169-192, (Mar. 5, 2004), 30 pages.

(56) References Cited

OTHER PUBLICATIONS

Ruchkin et al., "Modality-specific processing streams in verbal working memory: evidence from spatio-temporal patterns of brain activity," Cognitive Brain Research, vol. 6, pp. 95-113, Elsevier, (1997), 19 pages.
Rugg et al., "Event-related potentials and recognition memory," TRENDS in Cognitive Sciences, vol. 11, No. 6, www.sciencedirect.com, (May 3, 2007), 7 pages.
Rugg et al., "The ERP and cognitive psychology: conceptual issues," (Sep. 1996), 7 pages.
"User monitoring," Sapien Systems, available at http://web.archive.org/web/20030818043339/http://www.sapiensystems.com/eyetracking.html, (Aug. 18, 2003), 1 page.
Simon-Thomas et al, "Behavioral and Electrophysiological Evidence of a Right Hemisphere Bias for the Influence of Negative Emotion on Higher Cognition," Journal of Cognitive Neuroscience, pp. 518-529, Massachusetts Institute of Technology (2005), 12 pages.
Spencer, "Averaging, Detection, and Classification of Single-Trial ERPs," in Event-Related Potentials: A Methods Handbook, pp. 209-227, (Todd C. Handy, ed., 2005), 10 pages.
Arousal in Sport, in Encyclopedia of Applied Psychology, vol. 1, p. 159, retrieved from Google Books, (Spielberger, ed., Elsevier Academic Press, 2004), 1 page.
Srinivasan, "High-Resolution EEG: Theory and Practice," in Event-Related Potentials: A Methods Handbook, pp. 167-188, (Todd C. Handy, ed., 2005), 12 pages.
Sullivan et al., "A brain-machine interface using dry-contact, low-noise EEG sensors," In Proceedings of the 2008 IEEE International Symposium on Circuits and Systems, (May 18, 2008), 4 pages.
Sutherland, "Neuromarketing: What's it all about?" Retrieved from Max Sutherland's Weblog on Aug. 23, 2011, http://www.sutherlandsurvey.com/Column_pages/Neuromarketing_whats_it_all_about.htm, (Mar. 2007), 5 pages.
Swick et al., "Contributions of Prefrontal Cortex to Recognition Memory: Electrophysiological and Behavioral Evidence," Neuropsychology, vol. 13, No. 2, pp. 155-170, American Psychological Association, Inc. (1999), 16 pages.
Taheri et al., "A dry electrode for EEG recording," Electroencephalography and clinical Neurophysiology, pp. 376-383, Elsevier Science Ireland Ltd. (1994), 8 pages.
Talsma et al., "Methods for the Estimation and Removal of Artifacts and Overlap in ERP Waveforms," in Event-Related Potentials: A Methods Handbook, pp. 115-148, (Todd C. Handy, ed., 2005), 22 pages.
Vogel et al., "Electrophysiological Evidence for a Postperceptual Locus of Suppression During the Attentional Blink," Journal of Experimental Psychology: Human Perception and Performance, vol. 24, No. 6, pp. 1656-1674, (1998), 19 pages.
Voytek, et al., "Prefrontal cortex and basal ganglia contributions to visual working memory," PNAS Early Edition, www.pnas.org/cgi/doi/10.1073/pnas.1007277107, (2010), 6 pages.
Voytek, et al., "Hemicraniectomy: A New Model for Human Electrophysiology with High Spatio-temporal Resolution," Journal of Cognitive Neuroscience, vol. 22, No. 11, pp. 2491-2502, Massachusetts Institute of Technology, (Nov. 2009) 12 pages.
Wang, "Neurophysiological and Computational Principles of Cortical Rhythms in Cognition," Physiol Rev 90: pp. 1195-1268, American Physiological Society, www.prv.org, (2010), 75 pages.
Anonymous, "Functional magnetic resonance imaging," retrieved online from Wikipedia, the Free Encyclopedia on Aug. 23, 2011, at http://en.wikipedia.org/w/index.php?title=Functional_magnetic_resonance_imaging&oldid=319601772, (Oct. 13, 2009), 8 pages.
William, "Brain Signals to Control Movement of Computer Cursor," Blog article: Brain Signals to Control Movement of Computer Cursor, Artificial Intelligence, retrieved from the Internet on Aug. 17, 2011, http://whatisartificialintelligence.com/899/brain-signals-to-control-movement-of-computer-cursor/, (Feb. 17, 2010), 3 pages.

Woldorff, "Distortion of ERP averages due to overlap from temporally adjacent ERPs: Analysis and correction," Psychophysiology, Society for Psychophysiological Research, Cambridge University Press (1993), 22 pages.
Woodman, et al., "Serial Deployment of Attention During Visual Search," Journal of Experimental Psychology: Human Perception and Performance, vol. 29, No. 1, pp. 121-138, American Physiological Association (2003), 18 pages.
Yamaguchi, et al., "Rapid-Prefrontal-Hippocampal Habituation to Novel Events," The Journal of Neuroscience, pp. 5356-5363, Society for Neuroscience, (Apr. 29, 2004), 8 pages.
Yap et al., "TIMER: Tensor Image Morphing for Elastic Registration," NeuroImage, vol. 47, (May 3, 2009), 15 pages.
Yuval-Greenberg, et al., "Transient Induced Gamma-Bands Response in EEG as a Manifestation of Miniature Saccades," Neuron, vol. 58, pp. 429-441, Elsevier Inc. (May 8, 2008), 13 pages.
Ziegenfuss, "Neuromarketing: Advertising Ethical & Medical Technology," The Brownstone Journal, vol. XII, Boston University, pp. 69-73, (May 2005), 9 pages.
Zyga, "A Baseball Cap That Can Read Your Mind," PhysOrg.com, located at www.physorg.com/news130152277.html, (May 16, 2008), 11 pages.
Aaker et al., "Warmth in Advertising: Measurement, Impact, and Sequence Effects," Journal of Consumer Research, vol. 12, No. 4, pp. 365-381, (Mar. 1986), 18 pages.
Akam, et al., "Oscillations and Filtering Networks Support Flexible Routing of Information," Neuron, vol. 67, pp. 308-320, Elsevier, (Jul. 29, 2010), 13 pages.
Allen et al., "A Method for Removing Imaging Artifact from Continuous EEG Recorded during Functional MRI," Neuroimage, vol. 12, No. 2, 230-239, (Aug. 2000), 12 pages.
Ambler, "Salience and Choice: Neural Correlates of Shopping Decisions," Psychology & Marketing, vol. 21, No. 4, p. 247-261, Wiley Periodicals, Inc., doi: 10.1002/mar20004, (Apr. 2004), 16 pages.
Ambler et al., "Ads on the Brain; A Neuro-Imaging Comparison of Cognitive and Affective Advertising Stimuli," London Business School, Centre for Marketing Working Paper, No. 00-902, (Mar. 2000), 23 pages.
Badre et al. "Frontal Cortex and the Discovery of Abstract Action Rules," Neuron, vol. 66, pp. 315-326, Elsevier, (Apr. 29, 2010), 12 pages.
Bagozzi et al., "The Role of Emotions in Marketing," Journal of the Academy of Marketing Science, vol. 27, No. 2, pp. 184-206, Academy of Marketing Science (1999), 23 pages.
Barcelo, et al., "Prefrontal modulation of visual processing in humans," Nature Neuroscience, vol. 3, No. 4, Nature America, http://neurosci.nature.com, (Apr. 2000), 5 pages.
Barreto et al., "Physiologic Instrumentation for Real-time Monitoring of Affective State of Computer Users," WSEAS International Conference on Instrumentation, Measurement, Control, Circuits and Systems (IMCCAS), (2004), 6 pages.
Belch et al., "Psychophysiological and cognitive Responses to Sex in Advertising," Advances in Consumer Research, vol. 9, pp. 424-427, (1982), 6 pages.
Bimler et al., "Categorical perception of facial expressions of emotion: Evidence from multidimensional scaling," Cognition and Emotion, vol. 15(5), pp. 633-658 (2001), 26 pages.
Blakeslee, "If You Have a 'Buy Button' in Your Brain, What Pushes It?" The New York Times, www.nytimes.com, (Oct. 19, 2004), 3 pages.
Braeutigam, "Neuroeconomics—From neural systems to economic behavior," Brain Research Bulletin, vol. 67, pp. 355-360, Elsevier, (2005), 6 pages.
Buschman, et al., "Top-Down versus Bottom-Up Control of Attention in the Prefrontal and posterior Parietal Cortices," Science, vol. 315, www.sciencemag.org/cgi/content/full/315/5820/1860, American Association for the Advancement of Science, (2007), 4 pages.
Buschman, et al., "Serial, Covert Shifts of Attention during Visual Search Are Reflected by the Frontal Eye Fields and Correlated with Population Oscillations," Neuron, vol. 63, pp. 386-396, Elsevier, (Aug. 13, 2009), 11 pages.

(56) References Cited

OTHER PUBLICATIONS

Canolty, et al., "High Gamma Power Is Phase-Locked to Theta Oscillations in Human Neocortex," Science, vol. 313, www.sciencemag.org, (Sep. 15, 2006), 3 pages.
Cheng, et al. "Gender Differences in the Mu Rhythm of the Human Mirror-Neuron System," PLos ONE, vol. 3, Issue 5, www.plosone.org, (May 2008), 7 pages.
Clemons, "Resonance Marketing in the Age of the Truly Informed Consumer: Creating Profits through Differentiation and Delight," Wharton Information Strategy & Economics Blog 2, available at http://opim.wharton.upenn.edu/~clemons/blogs/resonanceblog.pdf, (Mar. 28, 2007), 8 pages.
Clifford, "Billboards That Look Back," The New York Times, NYTimes.com, available at http://www.nytimes.com/2008/05/31/business/media/31billboard.html, (May 31, 2008), 4 pages.
Crawford et al., "Self-generated happy and sad emotions in low and highly hypnotizable persons during waking and hypnosis: laterality and regional EEG activity differences," International Journal of Psychophysiology, vol. 24, pp. 239-266, (1996), 28 pages.
Davidson, et al., "The functional neuroanatomy of emotion and affective style," TRENDS in Cognitive Sciences, vol. 3, No. 1, (Jan. 1999), 11 pages.
de Gelder et al., "Categorical Perception of Facial Expressions: Categories and their Internal Structure," Cognition and Emotion, vol. 11(1), pp. 1-23 (1997), 23 pages.
D'Esposito, "From cognitive to neural models of working memory," Phil. Trans. R. Soc. B, doi: 10.1098/rstb.2007.2086, (Mar. 30, 2007), 12 pages.
Desmet, "Measuring Emotions: Development and Application of an Instrument to Measure Emotional Responses to Products," to be published in Funology: From Usability to Enjoyment, Kluwer Academic Publishers, (Blythe et al., eds., 2004), 13 pages.
Dien et al., "Application of Repeated Measures ANOVA to High-Dens Dataset: A Review and Tutorial," in Event-Related Potentials: A Methods Handbook, pp. 57-82, (Todd C. Handy, ed., 2005), 14 pages.
Edgar et al., "Digital Filters in ERP Research," in Event-Related Potentials: A Methods Handbook, pp. 85-113, (Todd C. Handy, ed., 2005), 15 pages.
EEG Protocols, "Protocols for EEG Recording," retrieved from the Internet on Aug. 23, 2011, http://www.q-metrx.com/EEGrecordingProtocols.pdf, (Nov. 13, 2007), 3 pages.
Engel et al., "Dynamic Predictions: Oscillations and Synchrony in Top-down Processing," Nature Reviews: Neuroscience, vol. 2, pp. 704-716, Macmillian Magazines Ltd., (Oct. 2001), 13 pages.
Filler, "MR Neurography and Diffusion Tensor Imaging: Origins, History & Clinical Impact of the first 50,000 Cases With an Assessment of Efficacy and Utility in a Prospective 5,000 Patient Study Group," Institute for Nerve Medicine, (Nov. 7, 2008), 56 pages.
Flinker et al, "Sub-centimeter language organization in the human temporal lobe," Brain and Language, Elsevier Inc., (2010), doi.org/10.1016/j.bandl.2010.09.009, 7 pages.
Fogelson et al., "Prefrontal cortex is critical for contextual processing: evidence from brain lesions," Brain: A Journal of Neurology, vol. 132, pp. 3002-3010, doi:10.1093/brain/awp230, (Aug. 27, 2009), 9 pages.
Friedman et al., "Event-Related Potential (ERP) Studies of Memory Encoding and Retrieval: A Selective Review," Microscopy Research and Technique 51:6-28, Wiley-Less, Inc. (2000), 23 pages.
Fries, "A mechanism for cognitive dynamics: neuronal communication through neuronal coherence," Trends in Cognitive Sciences, vol. 9, No. 10, pp. 474-480, Elsevier www.sciencedirect.com, (Oct. 2005), 7 pages.
Fuster, "Cortex and Memory: Emergence of a New Paradigm," Journal of Cognitive Neuroscience, vol. 21, No. 11, pp. 2047-2072, Massachusetts Institute of Technology, (2009), 26 pages.
Gaillard, "Problems and Paradigms in ERP Research," Biological Psychology, Elsevier Science Publishers B.V. (1988), 10 pages.
Gargiulo et al., "A Mobile EEG System With Dry Electrodes," (Nov. 2008), 4 pages.
Gazzaley et al., "Top-down Enhancement and Suppression of the Magnitude and Speed of Neural Activity," Journal of Cognitive Neuroscience, vol. 17, No. 3, pp. 507-517, Massachusetts Institute of Technology, (2005), 11 pages.
Griss et al., "Characterization of micromachined spiked biopotential electrodes", IEEE Transactions on Biomedical Engineering, vol. 49, No. 6, (Jun. 2002), 8 pages.
Haq, "This Is Your Brain on Advertising," BusinessWeek, Market Research, (Oct. 8, 2007), 4 pages.
Hartikainen et al., Manuscript Draft of "Emotionally arousing stimuli compete with attention to left hemispace," NeuroReport, (Sep. 8, 2007), 26 pages.
Hazlett et al., "Emotional Response to Television Commercials: Facial EMG vs. Self-Report," Journal of Advertising Research, (Apr. 1999), 17 pages.
Herrmann et al., "Mechanisms of human attention: event-related potentials and oscillations," Neuroscience and Biobehavioral Reviews, pp. 465-476, Elsevier Science Ltd., www.elsvevier.com/locate/neubiorev, (2001), 12 pages.
Hopf et al., "Neural Sources of Focused Attention in Visual Search," Cerebral Cortex, 10:1233-1241, Oxford University Press, (Dec. 2000), 9 pages.
Jung et al., "Analysis and Visualization of Single-Trial Event-Related Potentials," Human Brain Mapping vol. 14, 166-185 (2001), 20 pages.
Kay et al., "Identifying natural images from human brain activity," Nature, vol. 452, pp. 352-356, Nature Publishing Group, (Mar. 20, 2008), 5 pages.
Keren et al., "Saccadic spike potentials in gamma-band EEG: Characterization, detection and suppression," NeuroImage, http://dx.doi:10.1016/j.neuroimage.2009.10.057, (Oct. 2009), 16 pages.
Kishiyama et al., "Novelty Enhancements in Memory Are Dependent on Lateral Prefrontal Cortex," The Journal of Neuroscience, pp. 8114-8118, Society for Neuroscience (Jun. 24, 2009), 5 pages.
Kishiyama et al., "Socioeconomic Disparities Affect Prefrontal Function in Children," Journal of Cognitive Neuroscience pp. 1106-1115, Massachusetts Institute of Technology, (2008), 10 pages.
Klimesch, "EEG alpha and theta oscillations reflect cognitive and memory performance: a review and analysis," Brain Research Reviews, vol. 29, 169-195, (1999), 27 pages.
Knight, "Contribution of human hippocampal region to novelty detection," Nature, vol. 383, www.nature.com, (Sep. 19, 1996), 4 pages.
Knight, "Consciousness Unchained: Ethical Issues and the Vegetative and minimally Conscious State," The American Journal of Bioethics, 8:9, 1-2, http://dx.doi.org/10.1080/15265160802414524, (Sep. 1, 2008), 3 pages.
Knight et al., "Prefrontal cortex regulates inhibition and excitation in distributed neural networks," Acta Psychologica vol. 101, pp. 159-178, Elsevier (1999), 20 pages.
Knight, "Decreased Response to Novel Stimuli after Prefrontal Lesions in Man," Electroencephalography and Clinical Neurophysiology, vol. 59, pp. 9-20, Elsevier Scientific Publishers Ireland, Ltd., (1984), 12 pages.
Krakow et al., "Methodology: EEG-correlated fMRI," Functional Imaging in the Epilepsies, (Lippincott Williams & Wilkins, 2000), 17 pages.
Krugman, "Brain Wave Measures of Media Involvement," Journal of Advertising Research vol. 11, No. 1, 3-9 (Feb. 1971), 7 pages.
Non-Final Office Action, issued by the United States Patent and Trademark Office in connection with U.S. Appl. No. 12/546,586, dated Apr. 25, 2013, 34 pages.
Non-Final Office Action, issued by the United States Patent and Trademark Office in connection with U.S. Appl. No. 13/444,149, dated May 2, 2013, 27 pages.
Notice of Allowance, issued by the United States Patent and Trademark Office in connection with U.S. Appl. No. 12/056,190, dated May 8, 2013, 4 pages.
Notice of Allowance, issued by the United States Patent and Trademark Office in connection with U.S. Appl. No. 12/056,211, dated May 8, 2013, 5 pages.

(56) References Cited

OTHER PUBLICATIONS

Notice of Allowance, issued by the United States Patent and Trademark Office in connection with U.S. Appl. No. 12/135,074, dated May 8, 2013, 5 pages.
Notice of Allowance, issued by the United States Patent and Trademark Office in connection with U.S. Appl. No. 12/199,596, dated May 8, 2013, 7 pages.
Notice of Allowance, issued by the United States Patent and Trademark Office in connection with U.S. Appl. No. 13/569,711, dated May 14, 2013, 6 pages.
Notice of Allowance, issued by the United States Patent and Trademark Office in connection with U.S. Appl. No. 12/182,874, dated May 17, 2013, 6 pages.
Final Office Action, issued by the United States Patent and Trademark Office in connection with U.S. Appl. No. 12/778,828, dated May 23, 2013, 25 pages.
Office Communication to Applicant, issued by the United States Patent and Trademark Office in connection with U.S. Appl. No. 12/234,388, dated May 24, 2013, 2 pages.
Non-Final Office Action, issued by the United States Patent and Trademark Office in connection with U.S. Appl. No. 12/884,034, dated May 28, 2013, 12 pages.
Notice of Allowance, issued by the United States Patent and Trademark Office in connection with U.S. Appl. No. 12/135,074, dated May 31, 2013, 5 pages.
Notice of Allowance, issued by the United States Patent and Trademark Office in connection with U.S. Appl. No. 12/056,211, dated Jun. 3, 2013, 5 pages.
Notice of Allowance, issued by the United States Patent and Trademark Office in connection with U.S. Appl. No. 12/199,596, dated Jun. 3, 2013, 5 pages.
Notice of Allowance, issued by the United States Patent and Trademark Office in connection with U.S. Appl. No. 12/199,596, dated Jun. 11, 2013, 7 pages.
Notice of Allowance, issued by the United States Patent and Trademark Office in connection with U.S. Appl. No. 12/545,455, dated Jun. 11, 2013, 9 pages.
Notice of Allowance, issued by the United States Patent and Trademark Office in connection with U.S. Appl. No. 12/056,190, dated Jun. 13, 2013, 5 pages.
Office Communication to Applicant, issued by the United States Patent and Trademark Office in connection with U.S. Appl. No. 12/234,388, dated Jun. 13, 2013, 2 pages.
Notice of Allowance, issued by the United States Patent and Trademark Office in connection with U.S. Appl. No. 12/135,074, dated Jun. 21, 2013, 5 pages.
Non-Final Office Action, issued by the United States Patent and Trademark Office in connection with U.S. Appl. No. 13/105,774, dated Jun. 26, 2013, 10 pages.
English Translation of Office Action, issued by the Israeli Patent Office in connection with Patent Application No. 203176, dated Apr. 23, 2013, 1 page.
English Translation of Notice Prior to Allowance, issued by the Israeli Patent Office in connection with Patent Application No. 203176, dated Jun. 30, 2013, 1 page.
Merriam-Webster Online Dictionary, Definition for "Resonance," available at http://www.merriam-webster.com/dictionary/resonance, 4 pages.
Enghoff, Sigurd, Thesis: "Moving ICA and Time-Frequency Analysis in Event-Related EEG Studies of Selective Attention," Technical University of Denmark, (Dec. 1999), 54 pages.
Zhang, P., "Will You Use Animation on Your Web Pages?" Doing Business on the Internet: Opportunities and Pitfalls, C. Romm and F. Sudweeks (eds.), Spring-Verlag (1999), 17 pages.
Notice of Allowance, issued by the United States Patent and Trademark Office in connection with U.S. Appl. No. 12/182,874, dated Jul. 29, 2013, 6 pages.
Office Action, issued by the United States Patent and Trademark Office in connection with U.S. Appl. No. 12/546,586, dated Sep. 12, 2013, 13 pages.

Notice of Allowance, issued by the United States Patent and Trademark Office in connection with U.S. Appl. No. 12/199,596, dated Sep. 13, 2013, 7 pages.
Office Action, issued by the United States Patent and Trademark Office in connection with U.S. Appl. No. 12/113,870, dated Sep. 17, 2013, 11 pages.
Notice of Allowance, issued by the United States Patent and Trademark Office in connection with U.S. Appl. No. 12/778,828, dated Oct. 8, 2013, 11 pages.
English Translation of Office Action, issued by the Japanese Patent Office in connection with Patent Application No. 2010-523112, dated Jul. 30, 2013, 2 pages.
Decision to Grant Patent, issued by the Japanese Patent Office in connection with Patent Application No. 2010-506646, dated Aug. 6, 2013, 4 pages.
English Translation of Decision on Rejection, issued by the Chinese Patent Office in connection with Patent Application No. 200880017883.X, dated Aug. 5, 2013, 13 pages.
Extended European Search Report, issued by the European Patent Office in connection with European Application No. 08744383.4-2221/2130146, dated Jul. 27, 2011, 6 pages.
Extended European Search Report, issued by the European Patent Office in connection with European Application No. 10173095.0-2221, dated Dec. 17, 2010, 3 pages.
Extended European Search Report, issued by the European Patent Office in connection with European Application No. 10189294.1-2221, dated Mar. 21, 2011, 7 pages.
First Office Action, issued by the State Intellectual Property Office of P.R. China in connection with Patent Application No. 200880104982.1, dated Jan. 25, 2011, 15 pages.
First Office Action, issued by the State Intellectual Property Office of P.R. China in connection with Patent Application No. 2008801015007, dated May 25, 2011, 8 pages.
First Office Action, issued by the State Intellectual Property Office of P.R. China in connection with Patent Application No. 200880019166.0, dated Jul. 22, 2011, 16 pages.
Decision of Rejection, issued by the State Intellectual Property Office of P.R. China in connection with Patent Application No. 200880104982.1, dated Sep. 23, 2011, 10 pages.
Extended European Search Report, issued by the European Patent Office in connection with European Application No. 11006934.1-2221, dated Oct. 25, 2011, 5 pages.
First Office Action, issued by the State Intellectual Property Office of P.R. China in connection with Patent Application No. 200880017883.X, dated Nov. 30, 2011, 16 pages.
English Translation of Office Action, issued by the Israel Patent Office in connection with Patent Application No. 203176, dated Feb. 21, 2012, 2 pages.
English Translation of Office Action, issued by the Israel Patent Office in connection with Patent Application No. 203177, dated Mar. 1, 2012, 2 pages.
Second Office Action, issued by the State Intellectual Property Office of P.R. China in connection with Patent Application No. 200880101500.7, dated Apr. 5, 2012, 5 pages.
Second Office Action, issued by the State Intellectual Property Office of P.R. China in connection with Patent Application No. 200880019166.0, dated Jun. 5, 2012, 8 pages.
Second Office Action, issued by the State Intellectual Property Office of P.R. China in connection with Patent Application No. 200880104982.1, dated Jun. 29, 2012, 5 pages.
Second Office Action, issued by the State Intellectual Property Office of P.R. China in connection with Patent Application No. 200880017883.X, dated Aug. 10, 2012, 9 pages.
English Translation of Office Action, issued by the Israel Patent Office in connection with Patent Application No. 203176, dated Sep. 27, 2012, 1 pages.
English Translation of Office Action, issued by the Israel Patent Office in connection with Patent Application No. 203177, dated Sep. 27, 2012, 1 pages.
Office Action, issued by the Japanese Patent Office in connection with Patent Application No. 2010-501190, dated Oct. 5, 2012, 5 pages.

(56) References Cited

OTHER PUBLICATIONS

English Translation of Office Action, issued by the Japanese Patent Office in connection with Patent Application No. 2010-506646, dated Oct. 23, 2012, 3 pages.
English Translation of Third Office Action, issued by the State Intellectual Property Office of P.R. China in connection with Patent Application No. 200880101500.7, dated Nov. 21, 2012, 5 pages.
English Translation of Office Action, issued by the Israeli Patent Office in connection with Patent Application No. 201187, dated Nov. 27, 2012, 2 pages.
Extended European Search Report, issued by the European Patent Office in connection with European Application No. 08796890.5-2319/2170161, dated Dec. 7, 2012, 9 pages.
Notification to Grant Patent Right for Invention, issued by the State Intellectual Property Office of P.R. China in connection with Patent Application No. 200880104982.1, dated Jan. 14, 2013, 4 pages.
Extended European Search Report, issued by the European Patent Office in connection with European Application No. 08770372.4-1265/2152155, dated Feb. 6, 2013, 7 pages.
English Translation of Third Office Action, issued by the State Intellectual Property Office of P.R. China in connection with Patent Application No. 200880017883.X, dated Mar. 18, 2013, 8 pages.
Notification to Grant Patent Right for Invention, issued by the State Intellectual Property Office of P.R. China in connection with Patent Application No. 200880101500.7, dated Apr. 3, 2013, 2 pages.
Final Rejection, issued by the United States Patent and Trademark Office in connection with U.S. Appl. No. 12/056,211, dated Jul. 8, 2011, 16 pages.
Office Action, issued by the United States Patent and Trademark Office in connection with U.S. Appl. No. 12/056,211, dated Jan. 7, 2011, 19 pages.
Office Action issued by the United States Patent and Trademark Office in connection with U.S. Appl. No. 12/056,221, dated Apr. 15, 2011, 24 pages.
Final Rejection, issued by the United States Patent and Trademark Office in connection with U.S. Appl. No. 12/113,863, dated Jun. 9, 2011, 12 pages.
Office Action, issued by the United States Patent and Trademark Office in connection with U.S. Appl. No. 12/113,863, dated Dec. 27, 2010, 15 pages.
Final Rejection, issued by the United States Patent and Trademark Office in connection with U.S. Appl. No. 12/113,870, dated Apr. 21, 2011, 10 pages.
Office Action, issued by the United States Patent and Trademark Office in connection with U.S. Appl. No. 12/113,870, dated Dec. 3, 2010, 12 pages.
Office Action, issued by the United States Patent and Trademark Office in connection with U.S. Appl. No. 12/122,240, dated Jun. 10, 2011, 12 pages.
Final Rejection, issued by the United States Patent and Trademark Office in connection with U.S. Appl. No. 12/122,262, dated May 26, 2011, 15 pages.
Office Action, issued by the United States Patent and Trademark Office in connection with U.S. Appl. No. 12/122,262, dated Dec. 9, 2010, 13 pages.
Final Rejection, issued by the United States Patent and Trademark Office in connection with U.S. Appl. No. 12/135,066, dated Jan. 21, 2011, 16 pages.
Office Action, issued by the United States Patent and Trademark Office in connection with U.S. Appl. No. 12/135,066, dated Oct. 28, 2010, 14 pages.
Notice of Panel Decision from Pre-Appeal Brief Review, issued by the United States Patent and Trademark Office in connection with U.S. Appl. No. 12/135,066, on May 31, 2011, 2 pages.
Office Action, issued by the United States Patent and Trademark Office in connection with U.S. Appl. No. 12/135,074, dated Dec. 23, 2010, 14 pages.
Final Rejection, issued by the United States Patent and Trademark Office in connection with U.S. Appl. No. 12/135,074, dated Jun. 9, 2011, 10 pages.
Final Rejection, issued by the United States Patent and Trademark Office in connection with U.S. Appl. No. 12/182,874, dated Jul. 7, 2011, 14 pages.
Office Action, issued by the United States Patent and Trademark Office in connection with U.S. Appl. No. 12/182,874, dated Dec. 27, 2010, 17 pages.
Office Action, issued by the United States Patent and Trademark Office in connection with U.S. Appl. No. 12/199,557, dated Dec. 27, 2010, 14 pages.
Final Rejection, issued by the United States Patent and Trademark Office in connection with U.S. Appl. No. 12/199,557, dated Jun. 9, 2011, 12 pages.
Final Rejection, issued by the United States Patent and Trademark Office in connection with U.S. Appl. No. 12/199,583, dated Jun. 21, 2011, 14 pages.
Office Action, issued by the United States Patent and Trademark Office in connection with U.S. Appl. No. 12/199,583, dated Dec. 27, 2010, 17 pages.
Final Rejection, issued by the United States Patent and Trademark Office in connection with U.S. Appl. No. 12/199,596, dated Jun. 14, 2011, 13 pages.
Office Action, issued by the United States Patent and Trademark Office in connection with U.S. Appl. No. 12/199,596, dated Dec. 27, 2010, 17 pages.
Final Rejection, issued by the United States Patent and Trademark Office in connection with U.S. Appl. No. 12/200,813, dated Jul. 6, 2011, 13 pages.
Office Action, issued by the United States Patent and Trademark Office in connection with U.S. Appl. No. 12/200,813, dated Dec. 27, 2010, 14 pages.
Office Action, issued by the United States Patent and Trademark Office in connection with U.S. Appl. No. 12/234,372, dated Jun. 7, 2011, 10 pages.
Final Rejection, issued by the United States Patent and Trademark Office in connection with U.S. Appl. No. 12/135,069, dated Feb. 17, 2011, 32 pages.
Office Action, issued by the United States Patent and Trademark Office in connection with U.S. Appl. No. 12/135,069, dated Oct. 29, 2010, 21 pages.
Office Action, issued by the United States Patent and Trademark Office in connection with U.S. Appl. No. 12/357,315, dated May 4, 2011, 9 pages.
Office Action, issued by the United States Patent and Trademark Office in connection with U.S. Appl. No. 12/410,380, dated Jun. 7, 2011, 9 pages.
Office Action, issued by the United States Patent and Trademark Office in connection with U.S. Appl. No. 12/413,297, dated Jul. 18, 2011, 9 pages.
Office Action, issued by the United States Patent and Trademark Office in connection with U.S. Appl. No. 12/608,685, dated Jul. 12, 2011, 15 pages.
Office Action, issued by the United States Patent and Trademark Office in connection with U.S. Appl. No. 12/056,190, dated Aug. 10, 2011, 28 pages.
Office Action, issued by the United States Patent and Trademark Office in connection with U.S. Appl. No. 12/357,322, dated Aug. 23, 2011, 12 pages.
Office Action, issued by the United States Patent and Trademark Office in connection with U.S. Appl. No. 12/135,069, dated Aug. 26, 2011, 33 pages.
Restriction Requirement, issued by the United States Patent and Trademark Office in connection with U.S. Appl. No. 12/122,253, dated Sep. 2, 2011, 7 pages.
Office Action, issued by the United States Patent and Trademark Office in connection with U.S. Appl. No. 12/410,372, dated Sep. 12, 2011, 12 pages.
Restriction Requirement, issued by the United States Patent and Trademark Office in connection with U.S. Appl. No. 12/182,851, dated Sep. 12, 2011, 7 pages.
Office Action, issued by the United States Patent and Trademark Office in connection with U.S. Appl. No. 12/135,066, dated Sep. 29, 2011, 37 pages.

(56) References Cited

OTHER PUBLICATIONS

Restriction Requirement, issued by the United States Patent and Trademark Office in connection with U.S. Appl. No. 12/056,225, dated Oct. 3, 2011, 6 pages.
Office Action, issued by the United States Patent and Trademark Office in connection with U.S. Appl. No. 12/234,388, dated Oct. 12, 2011, 27 pages.
Office Action, issued by the United States Patent and Trademark Office in connection with U.S. Appl. No. 12/234,372, dated Oct. 13, 2011, 22 pages.
Office Action, issued by the United States Patent and Trademark Office in connection with U.S. Appl. No. 12/410,380, dated Oct. 19, 2011, 21 pages.
Office Action, issued by the United States Patent and Trademark Office in connection with U.S. Appl. No. 12/357,315, dated Oct. 26, 2011, 41 pages.
Office Action, issued by the United States Patent and Trademark Office in connection with U.S. Appl. No. 12/122,240, dated Oct. 27, 2011, 39 pages.
Final Rejection, issued by the United States Patent and Trademark Office in connection with U.S. Appl. No. 12/056,221, dated Nov. 28, 2011, 44 pages.
Office Action, issued by the United States Patent and Trademark Office in connection with U.S. Appl. No. 12/608,660, dated Dec. 7, 2011, 8 pages.
Office Action, issued by the United States Patent and Trademark Office in connection with U.S. Appl. No. 12/113,863, dated Dec. 22, 2011, 17 pages.
Office Action, issued by the United States Patent and Trademark Office in connection with U.S. Appl. No. 12/122,262, dated Dec. 22, 2011, 17 pages.
Office Action, issued by the United States Patent and Trademark Office in connection with U.S. Appl. No. 12/135,074, dated Dec. 22, 2011, 16 pages.
Office Action, issued by the United States Patent and Trademark Office in connection with U.S. Appl. No. 12/199,557, dated Dec. 22, 2011, 17 pages.
Office Action, issued by the United States Patent and Trademark Office in connection with U.S. Appl. No. 12/199,596, dated Dec. 22, 2011, 15 pages.
Office Action, issued by the United States Patent and Trademark Office in connection with U.S. Appl. No. 12/200,813, dated Dec. 22, 2011, 18 pages.
Office Action, issued by the United States Patent and Trademark Office in connection with U.S. Appl. No. 12/199,583, dated Dec. 29, 2011, 18 pages.
Final Rejection, issued by the United States Patent and Trademark Office in connection with U.S. Appl. No. 12/410,372, dated Jan. 3, 2012, 10 pages.
Final Rejection, issued by the United States Patent and Trademark Office in connection with U.S. Appl. No. 12/413,297, dated Jan. 4, 2012, 10 pages.
Office Action, issued by the United States Patent and Trademark Office in connection with U.S. Appl. No. 12/544,921, dated Jan. 9, 2012, 13 pages.
Office Action, issued by the United States Patent and Trademark Office in connection with U.S. Appl. No. 12/357,302, dated Jan. 17, 2012, 11 pages.
Office Action, issued by the United States Patent and Trademark Office in connection with U.S. Appl. No. 12/056,225, dated Jan. 20, 2012, 12 pages.
Final Rejection, issued by the United States Patent and Trademark Office in connection with U.S. Appl. No. 12/135,066, dated Jan. 24, 2012, 12 pages.
Office Action, issued by the United States Patent and Trademark Office in connection with U.S. Appl. No. 12/546,586, dated Feb. 1, 2012, 17 pages.
Restriction Requirement, issued by the United States Patent and Trademark Office in connection with U.S. Appl. No. 12/544,958, dated Feb. 10, 2012, 6 pages.
Final Rejection, issued by the United States Patent and Trademark Office in connection with U.S. Appl. No. 12/135,069, dated Feb. 14, 2012, 36 pages.
Final Rejection, issued by the United States Patent and Trademark Office in connection with U.S. Appl. No. 12/357,322, dated Feb. 14, 2012, 14 pages.
Office Action, issued by the United States Patent and Trademark Office in connection with U.S. Appl. No. 12/056,211, dated Feb. 16, 2012, 16 pages.
Final Rejection, issued by the United States Patent and Trademark Office in connection with U.S. Appl. No. 12/056,190, dated Feb. 17, 2012, 22 pages.
Office Action, issued by the United States Patent and Trademark Office in connection with U.S. Appl. No. 12/122,253, dated Feb. 17, 2012, 20 pages.
Office Action, issued by the United States Patent and Trademark Office in connection with U.S. Appl. No. 12/182,874, dated Feb. 17, 2012, 15 pages.
Office Action, issued by the United States Patent and Trademark Office in connection with U.S. Appl. No. 12/868,531, dated Mar. 1, 2012, 7 pages.
Office Action, issued by the United States Patent and Trademark Office in connection with U.S. Appl. No. 12/182,851, dated Mar. 14, 2012, 17 pages.
Office Action, issued by the United States Patent and Trademark Office in connection with U.S. Appl. No. 12/608,685, dated Mar. 29, 2012, 17 pages.
Office Action, issued by the United States Patent and Trademark Office in connection with U.S. Appl. No. 12/846,242, dated Mar. 29, 2012, 16 pages.
Office Action, issued by the United States Patent and Trademark Office in connection with U.S. Appl. No. 12/234,388, dated Apr. 6, 2012, 6 pages.
Office Action, issued by the United States Patent and Trademark Office in connection with U.S. Appl. No. 12/357,3158, dated Apr. 9, 2012, 17 pages.
Office Action, issued by the United States Patent and Trademark Office in connection with U.S. Appl. No. 12/544,958, dated May 2, 2012, 15 pages.
Notice of Allowance, issued by the United States Patent and Trademark Office in connection with U.S. Appl. No. 12/357,302, dated May 7, 2012, 11 pages.
Notice of Allowance, issued by the United States Patent and Trademark Office in connection with U.S. Appl. No. 12/868,531, dated May 8, 2012, 11 pages.
Notice of Allowance, issued by the United States Patent and Trademark Office in connection with U.S. Appl. No. 12/608,696, dated May 15, 2012, 6 pages.
Restriction Requirement, issued by the United States Patent and Trademark Office in connection with U.S. Appl. No. 12/545,455, dated Jun. 13, 2012, 5 pages.
Office Action, issued by the United States Patent and Trademark Office in connection with U.S. Appl. No. 12/056,225, dated Jun. 15, 2012, 9 pages.
Office Action, issued by the United States Patent and Trademark Office in connection with U.S. Appl. No. 12/544,934, dated Jun. 18, 2012, 11 pages.
Office Action, issued by the United States Patent and Trademark Office in connection with U.S. Appl. No. 12/135,066, dated Jun. 21, 2012, 10 pages.
Final Rejection, issued by the United States Patent and Trademark Office in connection with U.S. Appl. No. 12/608,660, dated Jul. 10, 2012, 14 pages.
Final Rejection, issued by the United States Patent and Trademark Office in connection with U.S. Appl. No. 12/608,685, dated Jul. 30, 2012, 15 pages.
Examiner's Answer, issued by the United States Patent and Trademark Office in connection with U.S. Appl. No. 12/410,372, dated Aug. 3, 2012, 8 pages.
Examiner's Answer, issued by the United States Patent and Trademark Office in connection with U.S. Appl. No. 12/410,380, dated Jun. 8, 2012, 12 pages.

(56) References Cited

OTHER PUBLICATIONS

Examiner's Answer, issued by the United States Patent and Trademark Office in connection with U.S. Appl. No. 12/234,372, dated May 23, 2012, 11 pages.
Advisory Action, issued by the United States Patent and Trademark Office in connection with U.S. Appl. No. 12/234,388, dated Aug. 28, 2012, 3 pages.
Office Action, issued by the United States Patent and Trademark Office in connection with U.S. Appl. No. 12/545,455, dated Aug. 29, 2012, 11 pages.
Office Action, issued by the United States Patent and Trademark Office in connection with U.S. Appl. No. 12/778,828, dated Aug. 30, 2012, 9 pages.
Office Action, issued by the United States Patent and Trademark Office in connection with U.S. Appl. No. 12/778,810, dated Aug. 31, 2012, 12 pages.
Notice of Allowance, issued by the United States Patent and Trademark Office in connection with U.S. Appl. No. 12/056,190, dated Sep. 17, 2012, 11 pages.
Notice of Allowance, issued by the United States Patent and Trademark Office in connection with U.S. Appl. No. 12/122,262, dated Sep. 17, 2012, 11 pages.
Final Rejection, issued by the United States Patent and Trademark Office in connection with U.S. Appl. No. 12/122,253, dated Sep. 17, 2012, 17 pages.
Examiner's Answer, issued by the United States Patent and Trademark Office in connection with U.S. Appl. No. 12/413,297, dated Sep. 18, 2012, 18 pages.
Final Rejection, issued by the United States Patent and Trademark Office in connection with U.S. Appl. No. 12/546,586, dated Sep. 18, 2012, 17 pages.
Notice of Allowance, issued by the United States Patent and Trademark Office in connection with U.S. Appl. No. 12/056,211, dated Sep. 19, 2012, 10 pages.
Notice of Allowance, issued by the United States Patent and Trademark Office in connection with U.S. Appl. No. 12/135,074, dated Sep. 19, 2012, 10 pages.
Notice of Allowance, issued by the United States Patent and Trademark Office in connection with U.S. Appl. No. 12/200,813, dated Sep. 20, 2012, 11 pages.
Notice of Allowance, issued by the United States Patent and Trademark Office in connection with U.S. Appl. No. 12/853,213, dated Sep. 7, 2012, 9 pages.
Notice of Allowance, issued by the United States Patent and Trademark Office in connection with U.S. Appl. No. 12/199,583, dated Sep. 26, 2012, 14 pages.
Notice of Allowance, issued by the United States Patent and Trademark Office in connection with U.S. Appl. No. 12/199,596, dated Sep. 27, 2012, 14 pages.
Notice of Allowance, issued by the United States Patent and Trademark Office in connection with U.S. Appl. No. 12/199,557, dated Sep. 28, 2012, 12 pages.
Notice of Allowance, issued by the United States Patent and Trademark Office in connection with U.S. Appl. No. 12/113,863, dated Oct. 1, 2012, 12 pages.
Office Action, issued by the United States Patent and Trademark Office in connection with U.S. Appl. No. 13/444,149, dated Oct. 4, 2012, 9 pages.
Final Office Action, issued by the United States Patent and Trademark Office in connection with U.S. Appl. No. 12/182,851, dated Oct. 4, 2012, 14 pages.
Office Action, issued by the United States Patent and Trademark Office in connection with U.S. Appl. No. 12/234,388, dated Oct. 5, 2012, 6 pages.
Notice of Allowance, issued by the United States Patent and Trademark Office in connection with U.S. Appl. No. 12/853,197, dated Oct. 16, 2012, 5 pages.
Notice of Allowance, issued by the United States Patent and Trademark Office in connection with U.S. Appl. No. 12/868,531, dated Oct. 22, 2012, 5 pages.
Final Office Action, issued by the United States Patent and Trademark Office in connection with U.S. Appl. No. 12/846,242, dated Nov. 29, 2012, 14 pages.
Notice of Allowance, issued by the United States Patent and Trademark Office in connection with U.S. Appl. No. 12/200,813, dated Oct. 30, 2012, 5 pages.
Notice of Allowance, issued by the United States Patent and Trademark Office in connection with U.S. Appl. No. 12/056,190, dated Nov. 2, 2012, 5 pages.
Restriction Requirement, issued by the United States Patent and Trademark Office in connection with U.S. Appl. No. 12/056,225, dated Nov. 2, 2012, 5 pages.
Final Office Action, issued by the United States Patent and Trademark Office in connection with U.S. Appl. No. 12/135,066, dated Nov. 13, 2012, 9 pages.
Notice of Allowance, issued by the United States Patent and Trademark Office in connection with U.S. Appl. No. 12/113,863, dated Nov. 16, 2012, 5 pages.
Notice of Allowance, issued by the United States Patent and Trademark Office in connection with U.S. Appl. No. 12/056,211, dated Nov. 21, 2012, 5 pages.
Notice of Allowance, issued by the United States Patent and Trademark Office in connection with U.S. Appl. No. 12/868,531, dated Nov. 23, 2012, 5 pages.
Office Action, issued by the United States Patent and Trademark Office in connection with U.S. Appl. No. 12/913,102, dated Dec. 7, 2012, 7 pages.
Final Office Action, issued by the United States Patent and Trademark Office in connection with U.S. Appl. No. 12/544,958, dated Dec. 10, 2012, 16 pages.
Notice of Allowance, issued by the United States Patent and Trademark Office in connection with U.S. Appl. No. 12/853,197, dated Dec. 20, 2012, 5 pages.
Notice of Allowance, issued by the United States Patent and Trademark Office in connection with U.S. Appl. No. 12/056,190, dated Dec. 21, 2012, 14 pages.
Notice of Allowance, issued by the United States Patent and Trademark Office in connection with U.S. Appl. No. 12/056,211, dated Dec. 21, 2012, 10 pages.
Notice of Allowance, issued by the United States Patent and Trademark Office in connection with U.S. Appl. No. 12/122,262, dated Dec. 21, 2012, 19 pages.
Notice of Allowance, issued by the United States Patent and Trademark Office in connection with U.S. Appl. No. 12/135,074, dated Dec. 21, 2012, 12 pages.
Notice of Allowance, issued by the United States Patent and Trademark Office in connection with U.S. Appl. No. 12/199,557, dated Dec. 21, 2012, 14 pages.
Notice of Allowance, issued by the United States Patent and Trademark Office in connection with U.S. Appl. No. 12/199,596, dated Dec. 21, 2012, 17 pages.
Notice of Allowance, issued by the United States Patent and Trademark Office in connection with U.S. Appl. No. 12/200,813, dated Dec. 21, 2012, 9 pages.
Notice of Allowance, issued by the United States Patent and Trademark Office in connection with U.S. Appl. No. 12/853,213, dated Dec. 21, 2012, 10 pages.
Notice of Allowance, issued by the United States Patent and Trademark Office in connection with U.S. Appl. No. 12/868,531, dated Dec. 26, 2012, 2 pages.
Notice of Allowance, issued by the United States Patent and Trademark Office in connection with U.S. Appl. No. 12/113,863, dated Dec. 31, 2012, 5 pages.
Notice of Allowance, issued by the United States Patent and Trademark Office in connection with U.S. Appl. No. 12/199,583, dated Dec. 31, 2012, 10 pages.
Final Office Action, issued by the United States Patent and Trademark Office in connection with U.S. Appl. No. 12/182,874, dated Jan. 4, 2013, 17 pages.
Notice of Allowance, issued by the United States Patent and Trademark Office in connection with U.S. Appl. No. 12/199,583, dated Jan. 11, 2013, 11 pages.

(56) References Cited

OTHER PUBLICATIONS

Final Office Action, issued by the United States Patent and Trademark Office in connection with U.S. Appl. No. 12/056,225, dated Jan. 11, 2013, 11 pages.
Recertified IDS and Interview Summary, issued by the United States Patent and Trademark Office in connection with Appl. No. 12/853,197, dated Jan. 16, 2013, 6 pages.
Notice of Allowance, issued by the United States Patent and Trademark Office in connection with U.S. Appl. No. 12/199,557, dated Jan. 29, 2013, 17 pages.
Notice of Allowance, issued by the United States Patent and Trademark Office in connection with U.S. Appl. No. 12/85,3197, dated Jan. 29, 2013, 11 pages.
Notice of Allowance, issued by the United States Patent and Trademark Office in connection with U.S. Appl. No. 12/056,190, dated Jan. 31, 2013, 5 pages.
Notice of Allowance, issued by the United States Patent and Trademark Office in connection with U.S. Appl. No. 12/113,863, dated Jan. 31, 2013, 5 pages.
Notice of Allowance, issued by the United States Patent and Trademark Office in connection with U.S. Appl. No. 12/135,074, dated Jan. 31, 2013, 10 pages.
Notice of Allowance, issued by the United States Patent and Trademark Office in connection with U.S. Appl. No. 12/199,583, dated Feb. 1, 2013, 11 pages.
Notice of Allowance, issued by the United States Patent and Trademark Office in connection with U.S. Appl. No. 12/200,813, dated Feb. 1, 2013, 5pages.
Notice of Allowance, issued by the United States Patent and Trademark Office in connection with U.S. Appl. No. 12/056,211, dated Feb. 4, 2013, 5 pages.
Notice of Allowance, issued by the United States Patent and Trademark Office in connection with U.S. Appl. No. 12/122,262, dated Feb. 5, 2013, 15 pages.
Notice of Allowance, issued by the United States Patent and Trademark Office in connection with U.S. Appl. No. 12/868,531, dated Feb. 5, 2013, 8 pages.
Notice of Allowance, issued by the United States Patent and Trademark Office in connection with U.S. Appl. No. 12/853,213, dated Feb. 5, 2013, 10 pages.
Notice of Allowance, issued by the United States Patent and Trademark Office in connection with U.S. Appl. No. 12/234,388, dated Feb. 15, 2013, 9 pages.
Notice of Allowance, issued by the United States Patent and Trademark Office in connection with U.S. Appl. No. 12/056,190, dated Feb. 14, 2013, 5 pages.
Notice of Allowance, issued by the United States Patent and Trademark Office in connection with U.S. Appl. No. 12/182,874, dated Apr. 16, 2013, 10 pages.
Notice of Allowance, issued by the United States Patent and Trademark Office in connection with U.S. Appl. No. 12/182,874, dated Apr. 22, 2013, 11 pages.
International Preliminary Report on Patentability, issued by the International Bureau of WIPO in connection with International Application No. PCT/US08/058264, dated Sep. 29, 2009, 1 page.
International Search Report, issued by the International Searching Authority in connection with International Application No. PCT/US08/058264, dated Aug. 1, 2008, 2 pages.
Written Opinion, issued by the International Searching Authority in connection with International Application No. PCT/US08/058264, dated Aug. 1, 2008, 5 pages.
International Preliminary Report on Patentability, issued by the International Bureau of WIPO in connection with International Application No. PCT/US08/062273, dated Nov. 3, 2009, 1 page.
International Search Report, issued by the International Searching Authority in connection with International Application No. PCT/US08/062273, dated Sep. 5, 2008, 2 pages.
Written Opinion, issued by the International Searching Authority in connection with International Application No. PCT/US08/062273, dated Sep. 5, 2008, 4 pages.
International Search Report, issued by the International Bureau in connection with International Application No. PCT/US08/062275, dated Sep. 22, 2008, 2 pages.
Written Opinion, issued by the International Bureau in connection with International Application No. PCT/US08/062275, dated Sep. 22, 2008, 6 pages.
International Preliminary Report on Patentability, issued by the International Bureau of WIPO in connection with International Application No. PCT/US08/063984, dated Nov. 17, 2009, 1 page.
International Search Report, issued by the International Bureau in connection with International Application No. PCT/US08/063984, dated Sep. 29, 2008, 3 pages.
Written Opinion, issued by the International Bureau in connection with International Application No. PCT/US08/063984, dated Sep. 29, 2008, 4 pages.
International Preliminary Report on Patentability, issued by the International Bureau of WIPO in connection with International Application No. PCT/US08/063989, dated Nov. 17, 2009, 1 page.
International Search Report, issued by the International Bureau in connection with International Application No. PCT/US08/063989, dated Jul. 17, 2008, 2 pages.
Written Opinion, issued by the International Bureau in connection with International Application No. PCT/US08/063989, dated Jul. 17, 2008, 4 pages.
International Preliminary Report on Patentability, issued by the International Bureau of WIPO in connection with International Application No. PCT/US08/066166, dated Dec. 7, 2009, 1 page.
International Search Report, issued by the International Bureau in connection with International Application No. PCT/US08/066166, dated Aug. 25, 2008, 2 pages.
Written Opinion, issued by the International Bureau in connection with International Application No. PCT/US08/066166, dated Aug. 25, 2008, 6 pages.
International Preliminary Report on Patentability, issued by the International Bureau of WIPO in connection with International Application No. PCT/US08/071639, dated Feb. 2, 2010, 1 page.
Written Opinion, issued by the International Bureau in connection with International Application No. PCT/US08/071639, dated Oct. 22, 2008, 4 pages.
International Preliminary Report on Patentability, issued by the International Bureau of WIPO in connection with International Application No. PCT/US08/074467, dated Mar. 2, 2010, 1 page.
International Search Report, issued by the International Bureau in connection with International Application No. PCT/US08/074467, dated Nov. 17, 2008, 2 pages.
Written Opinion, issued by the International Bureau in connection with International Application No. PCT/US08/074467, dated Nov. 17, 2008, 4 pages.
International Preliminary Report of Patentability, issued by the International Bureau in connection with International Application No. PCT/US10/021535, dated Jul. 26, 2011, 1 page.
International Search Report, issued by the International Bureau in connection with International Application No. PCT/US10/021535, dated Mar. 23, 2010, 3 pages.
Written Opinion, issued by the International Bureau in connection with International Application No. PCT/US10/021535, dated Mar. 23, 2010, 4 pages.
International Preliminary Report of Patentability, issued by the International Bureau in connection with International Application No. PCT/US09/065368, dated Jun. 23, 2011, 2 pages.
International Search Report, issued by the International Bureau in connection with International Application No. PCT/US09/065368, dated Jan. 21, 2010, 3 pages.
Written Opinion, issued by the International Bureau in connection with International Application No. PCT/US09/065368, dated Jan. 21, 2010, 7 pages.
International Preliminary Report on Patentability, issued by the International Bureau of WIPO in connection with International Application No. PCT/US08/062275, dated Nov. 3, 2009, 1 page.
International Search Report, issued by the International Bureau in connection with International Application No. PCT/US08/071639, dated Oct. 22, 2008, 3 pages.

(56) References Cited

OTHER PUBLICATIONS

Office Action, issued by the United States Patent and Trademark Office in connection with U.S. Appl. No. 13/730,511, dated Jan. 30, 2014, 6 pages.
Office Action, issued by the United States Patent and Trademark Office in connection with U.S. Appl. No. 13/730,550, dated Jan. 31, 2014, 5 pages.
Office Action, issued by the United States Patent and Trademark Office in connection with U.S. Appl. No. 13/965,805, dated Feb. 3, 2014, 15 pages.
Notice of Allowance, issued by the United States Patent and Trademark Office in connection with U.S. Appl. No. 13/444,149, dated Feb. 3, 2014, 5 pages.
Office Action, issued by the United States Patent and Trademark Office in connection with U.S. Appl. No. 12/113,870, dated Feb. 4, 2014, 12 pages.
Office Action, issued by the United States Patent and Trademark Office in connection with U.S. Appl. No. 12/546,586, dated Feb. 6, 2014, 17 pages.
Office Action, issued by the United States Patent and Trademark Office in connection with U.S. Appl. No. 13/730,564, dated Feb. 10, 2014, 14 pages.
Office Action, issued by the United States Patent and Trademark Office in connection with U.S. Appl. No. 112/884,034, dated Feb. 10, 2014, 18 pages.
Mehta, A. et al., "Reconsidering Recall and Emotion in Advertising", Journal of Advertising Research, (Mar. 2006), 49-56, 8 pages.
Cheung, Kwok-Wai, et al., "Mining Customer Product Ratings for Personalized Marketing," Decision Support Systems 35 (2003) 231-243, 13 pages.
Notice of Allowance, issued by the United States Patent and Trademark Office in connection with U.S. Appl. No. 13/730,550, dated May 27, 2014, 8 pages.
Notice of Allowance, issued by the United States Patent and Trademark Office in connection with U.S. Appl. No. 13/730,511, dated May 29, 2014, 8 pages.
Office Action, issued by the United States Patent and Trademark Office in connection with U.S. Appl. No. 12/608,660, dated Jun. 2, 2014, 13 pages.
Office Action, issued by the United States Patent and Trademark Office in connection with U.S. Appl. No. 12/122,253, dated Jun. 5, 2014, 25 pages.
Final Office Action, issued by the United States Patent and Trademark Office in connection with U.S. Appl. No. 12/113,870, dated Jul. 1, 2014, 16 pages.
Decision to Grant Patent, issued by the Japanese Patent Office in connection with Patent Application No. 2010-523112, dated Apr. 8, 2014, 4 pages.
English Translation of Office Action, issued by the Israel Patent Office in connection with Patent Application No. 201187, dated Apr. 23, 2014, 2 pages.
Darrow, Chester, "Psychological and psychophysiological significance of the electroencephalogram," Psychological Review (May 1947) 157-168, 12 pages.
Stamm, John, "On the Relationship between Reaction Time to Light and Latency of Blocking the Alpha Rhythm," Electroencephalography and Clinical Neurophysiology (Feb. 1952), 61-68, 8 pages.
Mizuki, Yashushi, et al., "Periodic Appearance of the Theta Rhythm in the Frontal Midline Area During Performance of a Mental Task,:" Electroencephalography and Clinical Neurophysiology (Aug. 1980), 345-351, 7 pages.
Final Office Action, issued by the United States Patent and Trademark Office in connection with U.S. Appl. No. 12/884,034, dated Oct. 23, 2013, 17 pages.
Notice of Allowance, issued by the United States Patent and Trademark Office in connection with U.S. Appl. No. 12/199,596, dated Nov. 6, 2013, 7 pages.
Final Office Action, issued by the United States Patent and Trademark Office in connection with U.S. Appl. No. 13/444,149, dated Nov. 19, 2013, 11 pages.

Non-Final Office Action, issued by the United States Patent and Trademark Office in connection with U.S. Appl. No. 12/122,253, dated Dec. 3, 2013, 16 pages.
Notice of Allowance, issued by the United States Patent and Trademark Office in connection with U.S. Appl. No. 12/199,596, dated Dec. 23, 2013, 7 pages.
Final Office Action, issued by the United States Patent and Trademark Office in connection with U.S. Appl. No. 13/105,774, dated Jan. 16, 2014, 11 pages.
English Translation of Office Action, issued by the Japanese Patent Office in connection with Patent Application No. 2010-520159, dated Oct. 1, 2013, 2 pages.
Extended European Search Report, issued by the European Patent Office in connection with European Application No. 08798799.6-1657/2180825, dated Nov. 4, 2013, 9 pages.
Coan et al., "Voluntary Facial Expression and Hemispheric Asymmetry Over the Frontal Cortex," Psycophysiology (Nov. 2001), 912-924, 14 pages.
Duchowski, "A Breadth-First Survey of Eye-tracking Applications," Beahavior Research Methods, Instruments, and Computers (Nov. 2002), 455-470, 16 pages.
Heo et al., "Wait! Why is it Not Moving? Attractive and Distractive Ocular Responses to Web Ads," Paper presented to AEJMC, (Aug. 2001) Washington, DC, available at http://www.psu.edu/dept/medialab/researchpage/newabstracts/wait.html, 3 pages.
Rothschild et al., "Predicting Memory for Components of TV Commercials from EEG," Journal of Consumer Research (Mar. 1990), p. 472-478, 8 pages.
Beaver, John D., et al., "Individual Differences in Reward Drive Predict Neural Responses to Images of Food", J. of Neuroscience, (May 10, 2006), 5160-5166, 7 pages.
Tapert, Susan F., et al., "Neural Response to Alcohol Stimuli in Adolescents With Alcohol Use Disorder", Arch Gen Psychiatry (Jul. 2003), 727-735, 9 pages.
Shandlen, Michael N. et al., "A Computational Analysis of the Relationship between Neuronal and Behavioral Responses to Visual Motion", The Journal of Neuroscience, (Feb. 15, 1996) 1486-1510, 25 pages.
Non-Final Office Action, issued by the United States Patent and Trademark Office in connection with U.S. Appl. No. 13/965,805, dated Aug. 6, 2014, 18 pages.
Non-Final Office Action, issued by the United States Patent and Trademark Office in connection with U.S. Appl. No. 13/730,511, dated Aug. 13, 2014, 4 pages.
Non-Final Office Action, issued by the United States Patent and Trademark Office in connection with U.S. Appl. No. 13/730,550, dated Aug. 14, 2014, 4 pages.
Non-Final Office Action, issued by the United States Patent and Trademark Office in connection with U.S. Appl. No. 13/730,564, dated Aug. 15, 2014, 15 pages.
Non-Final Office Action, issued by the United States Patent and Trademark Office in connection with U.S. Appl. No. 12/884,034, dated Aug. 21, 2014, 20 pages.
Non-Final Office Action, issued by the United States Patent and Trademark Office in connection with U.S. Appl. No. 12/608,685, dated Sep. 4, 2014, 16 pages.
Non-Final Office Action, issued by the United States Patent and Trademark Office in connection with U.S. Appl. No. 13/105,774, dated Sep. 18, 2014, 14 pages.
Final Office Action, issued by the United States Patent and Trademark Office in connection with U.S. Appl. No. 12/546,586, dated Sep. 29, 2014, 21 pages.
Decision to Grant Patent, issued by the Korean Patent Office in connection with Patent Application No. 10-2009-7022551, dated Aug. 13, 2014, 3 pages.
Ekman, P., Friesen, W., Measuring Facial Movement, Environmental Psychology and Nonverbal Behavior, 1 (1) (Fall 1976), pp. 56-75, 20 pages.
Ekman, P., Friesen, W.V., *Facial Action Coding System: A Technique for Measurement of Facial Movement*, Consulting Psychologists Press, Palo Alto, Calif. (1978).

(56) References Cited

OTHER PUBLICATIONS

Ekman, P., Friesen, W., *Unmasking the Face—A Guide to Recognizing Emotions from Facial Clues*, Prentice-Hall, Inc., Englewood Cliffs, N.J. (1979).
Ekman, P., Friesen, W., Ancoli, S., Facial Signs of Emotional Experience, J. Personality & Social Psychology, 39(6) (Dec. 1980), pp. 1125-1134, 10 pages.
Izard, C. E., *The Maximally Discriminative Facial Movement Coding System*, (Rev. ed.), Instructional Resources Center, University of Delaware, Newark, Del. (1983).
Izard, C., Dougherty, L., Hembree, E., *A System for Identifying Affect Expressions by Holistic Judgments (AFFEX)*, Instructional Resources Center, University of Delaware, Newark, Del. (1983).
Jia, X., Nixon, M.S., Extending the Feature Set for Automatic Face Recognition, International Conference on Image Processing and Its Applications (Apr. 7-9, 1992), 6 pages.
Lisetti, C., Nasoz, F., Using Noninvasive Wearable Computers to Recognize Human Emotions from Physiological Signals, EURASIP J. Applied Signal Processing, (Sep. 11, 2004), pp. 1672-1687, 16 pages.
Final Office Action, issued by the United States Patent and Trademark Office in connection with U.S. Appl. No. 13/708,344, dated Nov. 20, 2015, 28 pages.
Translation of Reexamination Decision, issued by the Chinese Patent Office in connection with Patent Application No. 200880017883.X, dated Nov. 13, 2015, 1 page.
Examiner's Answer, issued by the United States Patent and Trademark Office in connection with U.S. Appl. No. 12/113,870, dated Jul. 30, 2015, 14 pages.
Examiner's Answer, issued by the United States Patent and Trademark Office in connection with U.S. Appl. No. 12/122,253, dated Aug. 4, 2015, 30 pages.
Non-Final Office Action, issued by the United States Patent and Trademark Office in connection with U.S. Appl. No. 14/177,698, dated Aug. 19, 2015, 12 pages.
Examiner's Answer, issued by the United States Patent and Trademark Office in connection with U.S. Appl. No. 12/546,586, dated Sep. 11, 2015, 7 pages.
Final Office Action, issued by the United States Patent and Trademark Office in connection with U.S. Appl. No. 13/730,550, dated Sep. 2, 2015, 5 pages.
Non-Final Office Action, issued by the United States Patent and Trademark Office in connection with U.S. Appl. No. 12/410,380, dated Sep. 10, 2015, 15 pages.
Advisory Action, issued by the United States Patent and Trademark Office in connection with U.S. Appl. No. 12/884,034, dated Sep. 16, 2015, 3 pages.
Non-Final Office Action, issued by the United States Patent and Trademark Office in connection with U.S. Appl. No. 13/708,525, dated Sep. 30, 2015, 12 pages.
Non-Final Office Action, issued by the United States Patent and Trademark Office in connection with U.S. Appl. No. 13/965,805, dated Sep. 30, 2015, 7 pages.
Decision on Appeal, issued by the United States Patent and Trademark Office in connection with U.S. Appl. No. 12/122,253, dated Mar. 31, 2017, 37 pages.
Non-Final Office Action, issued by the United States Patent and Trademark Office in connection with U.S. Appl. No. 13/708,525, dated Apr. 27, 2017, 45 pages.
Examiner's Answer, issued by the United States Patent and Trademark Office in connection with U.S. Appl. No. 12/410,372, dated May 25, 2017, 2017, 9 pages.
Decision on Appeal, issued by the United States Patent and Trademark Office in connection with U.S. Appl. No. 12/546,586, dated Jun. 5, 2017, 39 pages.
Communication Pursuant to Article 94(3), issued by the European Patent Office in connection with European Application No. 08744383.4-1958, dated Apr. 19, 2017, 6 pages.
Final Office Action, issued by the United States Patent and Trademark Office in connection with U.S. Appl. No. 13/945,357, dated Nov. 1, 2016, 22 pages.
Advisory Action, issued by the United States Patent and Trademark Office in connection with U.S. Appl. No. 12/410,372, dated Nov. 7, 2016, 3 pages.
Examiner's Answer, issued by the United States Patent and Trademark Office in connection with U.S. Appl. No. 12/234,372, dated Nov. 14, 2016, 18 pages.
Examiner's Answer, issued by the United States Patent and Trademark Office in connection with U.S. Appl. No. 12/608,685, dated Nov. 14, 2016, 10 pages.
Final Office Action, issued by the United States Patent and Trademark Office in connection with U.S. Appl. No. 12/884,034, dated Nov. 29, 2016, 27 pages.
First Examination Report, issued by the European Patent Office in connection with European Application No. 08796890.5, dated Sep. 29, 2016, 4 pages.
Non-Final Office Action, issued by the United States Patent and Trademark Office in connection with U.S. Appl. No. 14/177,698, dated Oct. 24, 2014, 13 pages.
Advisory Action, issued by the United States Patent and Trademark Office in connection with U.S. Appl. No. 12/546,586, dated Dec. 22, 2014, 3 pages.
English Translation of Notification of Provisional Rejection, issued by the Korean Patent Office in connection with Patent Application No. 10-2010-7001406, dated Oct. 21, 2014, 1 page.
Advisory Action, issued by the United States Patent and Trademark Office in connection with U.S. Appl. No. 13/708,344, dated Oct. 2, 2017, 5 pages.
Final Office Action, issued by the United States Patent and Trademark Office in connection with U.S. Appl. No. 13/945,357, dated Oct. 20, 2017, 16 pages.
Advisory Action, issued by the United States Patent and Trademark Office in connection with U.S. Appl. No. 13/708,525, dated Oct. 26, 2017, 4 pages.
Non-Final Office Action, issued by the United States Patent and Trademark Office in connection with U.S. Appl. No. 15/299,752, dated Nov. 3, 2017, 131 pages.
Non-Final Office Action, issued by the United States Patent and Trademark Office in connection with U.S. Appl. No. 12/884,034, dated Nov. 15, 2017, 49 pages.
Non-Final Office Action, issued by the United States Patent and Trademark Office in connection with U.S. Appl. No. 12/410,380, dated Jun. 17, 2016, 20 pages.
Notice of Allowance, issued by the United States Patent and Trademark Office in connection with U.S. Appl. No. 12/608,660, dated Jul. 29, 2016, 67 pages.
Examiner's Answer, issued by the United States Patent and Trademark Office in connection with U.S. Appl. No. 13/730,550, dated Jul. 27, 2016, 20 pages.
Advisory Action, issued by the United States Patent and Trademark Office in connection with U.S. Appl. No. 12/234,372, dated Aug. 8, 2016, 3 pages.
Non-Final Office Action, issued by the United States Patent and Trademark Office in connection with U.S. Appl. No. 12/413,297, dated Aug. 16, 2016, 5 pages.
Final Office Action, issued by the United States Patent and Trademark Office in connection with U.S. Appl. No. 12/410,372, dated Aug. 25, 2016, 61 pages.
English Translation of Notification of Provisional Rejection, issued by the Korean Patent Office in connection with Patent Application No. 10-2010-7001406, dated Jul. 27, 2016, 4 pages.
Final Office Action, issued by the United States Patent and Trademark Office in connection with U.S. Appl. No. 12/410,380, dated Mar. 22, 2016, 27 pages.
Final Office Action, issued by the United States Patent and Trademark Office in connection with U.S. Appl. No. 12/608,685, dated Mar. 30, 2016, 23 pages.
Advisory Action, issued by the United States Patent and Trademark Office in connection with U.S. Appl. No. 13/708,525, dated Apr. 6, 2016, 3 pages.

(56) References Cited

OTHER PUBLICATIONS

Examiner's Answer, issued by the United States Patent and Trademark Office in connection with U.S. Appl. No. 13/730,564, dated Apr. 8, 2016, 7 pages.
Final Office Action, issued by the United States Patent and Trademark Office in connection with U.S. Appl. No. 13/965,805, dated Apr. 21, 2016, 33 pages.
Final Office Action, issued by the United States Patent and Trademark Office in connection with U.S. Appl. No. 12/234,372, dated May 12, 2016, 61 pages.
Non-Final Office Action, issued by the United States Patent and Trademark Office in connection with U.S. Appl. No. 12/884,034, dated May 20, 2016, 69 pages.
Non-Final Office Action, issued by the United States Patent and Trademark Office in connection with U.S. Appl. No. 13/945,357, dated May 20, 2016, 22 pages.
M. Corbetta et al., "Control of Goal-Directed and Stimulus-Driven Attention in the Brain," Nature Reviews Neuroscience, vol. 3, pp. 201-215 (Mar. 2002), 15 pages.
Becker, "A Study of Web Usability for Older Adults Seeking Online Health Resources," ACM Transactions on Computer-Human Interaction, vol. 11, No. 4, pp. 387-406 (Dec. 2004), 20 pages.
Final Office Action, issued by the United States Patent and Trademark Office in connection with U.S. Appl. No. 13/708,344, dated Jun. 29, 2017, 38 pages.
Non-Final Office Action, issued by the United States Patent and Trademark Office in connection with U.S. Appl. No. 13/945,357, dated Jul. 6, 2017, 17 pages.
Decision on Appeal, issued by the United States Patent and Trademark Office in connection with U.S. Appl. No. 12/113,870, dated Jul. 13, 2017, 12 pages.
Final Office Action, issued by the United States Patent and Trademark Office in connection with U.S. Appl. No. 13/708,525, dated Aug. 14, 2017, 38 pages.
Examiner's Answer, issued by the United States Patent and Trademark Office in connection with U.S. Appl. No. 12/410,380, dated Aug. 18, 2017, 2017, 11 pages.
Non-Final Office Action, issued by the United States Patent and Trademark Office in connection with U.S. Appl. No. 12/546,586, dated Sep. 19, 2017, 43 pages.
Notice of Allowance, issued by the United States Patent and Trademark Office in connection with U.S. Appl. No. 12/113,870, dated Sep. 26, 2017, 51 pages.
Summons to Attend Oral Proceedings Pursuant to Rule 115(1) EPC, issued by the European Patent Office in connection with European Patent Application No. 08796890.5, on Jul. 3, 2017, 3 pages.
English Translation of First Examination Report, issued by the Indian Patent Office in connection with Indian Patent Application No. 6145/CHENP/2009, dated Aug. 16, 2017, 6 pages.
Final Office Action, issued by the United States Patent and Trademark Office in connection with U.S. Appl. No. 12/410,380, dated Dec. 15, 2016, 31 pages.
Non-Final Office Action, issued by the United States Patent and Trademark Office in connection with U.S. Appl. No. 13/708,344, dated Jan. 26, 2017, 52 pages.
Examiner's Answer, issued by the United States Patent and Trademark Office in connection with U.S. Appl. No. 13/965,805, dated Jan. 31, 2017, 25 pages.
Final Office Action, issued by the United States Patent and Trademark Office in connection with U.S. Appl. No. 12/413,297, dated Feb. 9, 2017, 7 pages.
Advisory Action, issued by the United States Patent and Trademark Office in connection with U.S. Appl. No. 12/884,034, dated Mar. 2, 2017, 14 pages.
English Translation of Notice Prior to Allowance, issued by the Israeli Patent Office in connection with Patent Application No. 201187, dated Feb. 14, 2017, 1 page.
Decision on Appeal, issued by the United States Patent and Trademark Office in connection with U.S. Appl. No. 12/410,380, on Mar. 30, 2015, 6 pages.
Decision on Appeal, issued by the United States Patent and Trademark Office in connection with U.S. Appl. No. 12/234,372, on Jun. 15, 2015, 5 pages.
Decision on Appeal, issued by the United States Patent and Trademark Office in connection with U.S. Appl. No. 12/410,372, on Sep. 22, 2015, 6 pages.
Non-Final Office Action, issued by the United States Patent and Trademark Office in connection with U.S. Appl. No. 12/234,372, dated Sep. 23, 2015, 16 pages.
Decision on Appeal, issued by the United States Patent and Trademark Office in connection with U.S. Appl. No. 12/413,297, on Nov. 27, 2015, 5 pages.
Non-Final Office Action, issued by the United States Patent and Trademark Office in connection with U.S. Appl. No. 12/546,586, dated Dec. 28, 2017, 23 pages.
Decision on Appeal, issued by the United States Patent and Trademark Office in connection with U.S. Appl. No. 12/608,685, on Jan. 29, 2018, 11 pages.
English Translation of Office Action, issued by the Japanese Patent Office in connection with Patent Application No. 2010-501190, dated Oct. 2, 2012, 10 pages.
Extended European Search Report, issued by the European Patent Office in connection with European Application No. 08747389.8-1952, dated Sep. 25, 2015, 6 pages.
English Translation of First Examination Report, issued by the Indian Patent Office in connection with Indian Patent Application No. 4438/KOLNP/2009, dated Sep. 25, 2017, 7 pages.
Kamba et al., "The Krakatoa Chronicle—An Interactive, Personalized, Newspaper on the Web," available at: http://www.w3.org/Conferences/WWW4/Papers/93/ (last accessed Nov. 2, 2015), 15 pages.
Ehrenberg et al., "Understanding Brand Performance Measures: Using Dirichlet Benchmarks," 2004, Journal of Business Research, vol. 57, pp. 1307-1325, 19 pages.
Leeflang et al., "Building Models for Marketing Decisions," 2000, Springer Science + Business Media, pp. 192-235, 482-521, 86 pages.
Bhattacharya, "Is your brand's loyalty too much, too little, or just right?: Explaining deviations in loyalty from the Dirichlet norm," 1997, International Journal of Research in Marketing, vol. 14, pp. 421-435, 15 pages.
Nikolaeva et al., "The Moderating Role of Consumer and Product Characteristics on the Value of Customized On-Line Recommendations," 2006, International Journal of Electronic Commerce, vol. 11, No. 2, pp. 101-123, 24 pages.
Ehrenberg, "New Brands and the Existing Market," 1991, International Journal of Market Research, vol. 33, No. 4, 10 pages.
Foxall, "The Substitutability of Brands," 1999, Managerial and Decision Economics, vol. 20, pp. 241-257, 17 pages.
Pammer et al., "Forecasting the Penetration of a New Product—A Bayesian Approach," 2000, Journal of Business and Economic Statistics, vol. 18, No. 4, pp. 428-435, 8 pages.
Rungie et al., "Calculation of Theoretical Brand Performance Measures from the Parameters of the Dirichlet Model," 2004, Marketing Bulletin, Massey University, 15, Technical Note 2, pp. 1-19, 20 pages.
Uncles et al., "Patterns of Buyer Behavior: Regularities, Models, and Extensions," 1995, Marketing Science, vol. 14, No. 3, pp. G71-G78, 9 pages.
Boltz, "The cognitive processing of film and musical soundtracks," Haverford College, Haverford, Pennsylvania, 2004, 32 (7), 1194-1205, 12 pages.
Christie et al., "Autonomic specificity of discrete emotion and dimensions of affective space: a multivariate approach," International Journal of Psychophysiology, 51 (2004) 143-153, 11 pages.
Coombes et al., "Emotion and movement: Activation of defensive circuitry alters the magnitude of a sustained muscle contraction," University of Florida, USA, Neuroscience Letters 396 (2006) 192-196, 5 pages.
Cryer et al. "Pull the Plug on Stress," Harvard Business Review, Jul. 2003, 8 pages.
Demaree et al., "Predicting facial valence to negative stimuli from resting RSA: Not a function of active emotion regulation," Cogni-

(56) References Cited

OTHER PUBLICATIONS tion and Emotion vol. 20, Issue 2, 2006, pp. 161-176, published on Sep. 9, 2010, http://www.tandfonline.com/doi/abs/10.1080/02699930500260427, 6 pages. (Abstract provided).
Elkman et al., "Autonomic Nervous System Activity Distinguishes among Emotions," Science, New Series, vol. 221, No. 4616. (Sep. 16, 1983), pp. 1208-1210, http://links.jstor.org/sici?sici=0036-8075%2819830916%293%3A221%3A4616%3C1208%3AANSADA%3E2.0.CO%3B2-H, 5 pages.
Elton, "Measuring emotion at the symphony," The Boston Globe, Apr. 5, 2006, http://www.psych.mcgill.ca/labs/levitin/media/measuring_emotion_boston.html, 3 pages.
Goldberg, "Getting wired could help predict emotions," The Boston Globe, Jun. 13, 2005, http://www.boston.com/yourlife/health/mental/articles/2005/06/13/getting_wired_could_help_predict_emotions/?page=full, 4 pages.
Gomez et al., "Respiratory Responses Associated with Affective Processing of Film Stimuli," Biological Psychology, vol. 68, Issue 3, Mar. 2005, pp. 223-235, 2 pages. (Abstract provided).
Hall, "Is cognitive processing the right dimension," World Advertising Research Center, Jan. 2003, 3 pages.
Hall, "On Measuring the Power of Communications," Journal of Advertising Research, 44, pp. 1-11, doi:10.1017/S0021849904040139, (2004), 1 page. (Abstract provided).
Hall, "Research and strategy: a fall from grace," ADMAP, Issue 443, pp. 18-20, 2003, 1 page. (Abstract provided).
Hubert et al., "Autonomic, neuroendocrine, and subjective responses to emotion-inducing film stimuli," Int J Psychophysiol, Aug. 1991, 2 pages. (Abstract provided).
Levenson et al., "Emotion and Autonomic Nervous System Activity in the Minangkabau of West Sumatra," Department of Psychology, University of California, Berkeley, Journal of Personality and Social Psychology, 1992, 2 pages. (Abstract provided).
Marci et al., "The effect of emotional distance on psychophysiologic concordance and perceived empathy between patient and interviewer," Applied Psychophysiology and Biofeedback, Jun. 2006, vol. 31, issue 2, 31:115-129, 8 pages. (Abstract provided).
McCraty et al., "Analysis of twenty-four hour heart rate variability in patients with panic disorder," Biological Psychology, vol. 56, Issue 2, Jun. 2001, pp. 131-150, 1 page. (Abstract provided).
McCraty et al., "Electrophysiological Evidence of Intuition: Part 1. The Surprising Role of the Heart," The Journal of Alternative and Complementary Medicine, vol. 10, No. 1, 2004, pp. 133-143, Mary Ann Liebert, Inc., 12 pages.
McCraty et al., "Electrophysiological Evidence of Intuition: Part 2. A System-Wide Process?," The Journal of Alternative and Complementary Medicine, vol. 10, No. 2, 2004, pp. 325-336, Mary Ann Liebert, Inc., 12 pages.
McCraty et al., "The Effects of Different Types of Music on Mood, Tension, and Mental Clarity," Original Research, Alternative Therapies, Jan. 1998, vol. 4., No. 1, pp. 75-84, 10 pages.
McCraty et al., "The Effects of Emotions on Short-Term Power Spectrum Analysis of Heart Rate Variability," American Journal of Cardiology, vol. 76, No. 14, Nov. 15, 1995, pp. 1089-1093, 6 pages.
McCraty et al., "The Impact of a New Emotional Self-Management Program on Stress, Emotions, Heart Rate Variability, DHEA and Cortisol," Integrative Physiological and Behavioral Science, Apr.-Jun. 1998, vol. 33, No. 2, 151-170, 20 pages.
McCraty et al., "The Impact of an Emotional Self-Management Skills Course on Psychosocial Functioning and Autonomic Recovery to Stress in Middle School Children," Integrative Physiological and Behavioral Science, Oct.-Dec. 1999, vol. 34, No. 4, 246-268, 23 pages.
Melillo, "Inside the Consumer Mind; What Neuroscience Can Tell Us About Marketing," Adweek, Public Citizen's Commercial Alert, Jan. 16, 2006, http://www.adweek.com/news/advertising/inside-consumer-mind-83549, 8 pages.
Miller et al., "Influence of Specific Emotional States on Autonomic Reactivity and Pulmonary Function in Asthmatic Children," Journal of the American Academy of Child & Adolescent Psychiatry, vol. 36, Issue 5, May 1997, pp. 669-677, 3 pages. (Abstract provided).
Murphy et al., "The Heart Reinnervates After Transplantation," Official Journal of the Society of Thoracic Surgeons and the Southern Thoracic Surgical Association, Jun. 2000, vol. 69, Issue 6, pp. 1769-1781, 13 pages.
Rosenberg, "Emotional R.O.I.," The Hub, May/Jun. 2006, pp. 24-25, 2 pages.
Tiller et al., "Cardiac Coherence: A New, Noninvasive Measure of Autonomic Nervous System Order," Alternative Therapies, Jan. 1996, vol. 2, No. 1, 14 pages.
Umetani et al. "Twenty-Four Hour Time Domain Heart Rate Variability and Heart Rate: Relations to Age and Gender Over Nine Decades," J Am Coll Cardiol, Mar. 1, 1998, pp. 593-601, 9 pages.
Von Leupoldt et al., "Emotions in a Body Plethysmograph," Journal of Psychophysiology (2004), 18, pp. 170-176, 1 page. (Abstract provided).
Kallman, "Effect of Blank Time on Picture Recognition," The American Journal of Psychology, vol. 97, No. 3 (Autumn, 1984), pp. 399-406, 4 pages. (Abstract provided).
Larose, *Data Mining Methods and Models*, Department of Mathematical Sciences, Central Connecticut State University, www.dbeBooks.com—An Ebook Library, published by John Wiley & Sons, Inc., 2006, 340 pages.
Han et al., *Data Mining: Concepts and Techniques*, $2^{nd}$ Edition, Elsevier, 2006, 772 pages.
Liu et al., *Web Data Mining: Exploring Hyperlinks, Contents, and Usage Data*, Springer Science & Business Media, 2007, 532 pages.
Berry et al., *Data Mining Techniques: For Marketing, Sales, and Customer Support*, Wiley Publishing Inc., Jun. 1997, 464 pages.
Horovitz, "Watching Ads is Real Science Research Companies Monitor Physiological Reactions to Commercials to Determine Their Effectiveness," Los Angeles Times, Sep. 1, 1991, 3 pages.
Sung et al., "Wearable feedback systems for rehabilitation," Journal of NeuroEngineering and Rehabilitation, 2005, 12 pages.
Jaffe, *Casting for Big Ideas*, Adweek Magazine Series, Book 8, 2003, 256 page.
Hall "A New Model for Measuring Advertising Effectiveness," J. Advertising Research, vol. 42(2) (Mar./Apr. 2002), 1 page. (Abstract provided).
Hall, "Advertising as a Factor of Production," ADMAP, 2003, pp. 20-23, 1 page. (Abstract provided).
Ranii, "Adding Science to Gut Check," The News & Observer, D3 (Apr. 6, 2005), 1 page. (Abstract provided).
McCraty et al., "Impact of a Workplace Stress Reduction Program on Blood Pressure and Emotional Health in Hypertensive Employees", The Journal of Alternative and Complementary Medicine, vol. 9, No. 3, 2003, pp. 355-369, Mary Ann Liebert, Inc., 15 pages.
Knutson et al., "Neural Predictors of Purchases," Neuron vol. 53 (Jan. 4, 2007), pp. 147-156, 10 pages.
Schaefer et al., "Neural Correlates of Culturally Familiar Brands of Car Manufacturers," NeuroImage, vol. 31 (2006), pp. 861-865, 5 pages.
Aharon et al., "Beautiful Faces Have Variable Reward Value: fMRI and Behavorial Evidence," Neuron, vol. 32 (2001), pp. 537-551, 15 pages.
Hall, "A New Model for Measuring Advertising Effectiveness," Journal of Advertising Research, Mar.-Apr. 2002, 10 pages.
Ganel et al., "The Relationship Between fMRI Adapation and Repetition Priming," NeuroImage, Jul. 18, 2006, pp. 1434-1440, 9 pages.
Non-Final Office Action, issued by the United States Patent and Trademark Office in connection with U.S. Appl. No. 12/608,685, dated Dec. 17, 2015, 14 pages.
Notice of Allowance, issued by the United States Patent and Trademark Office in connection with U.S. Appl. No. 14/177,698, dated Jan. 14, 2016, 35 pages.
Non-Final Office Action, issued by the United States Patent and Trademark Office in connection with U.S. Appl. No. 12/608,660, dated Jan. 22, 2016, 38 pages.
Final Office Action, issued by the United States Patent and Trademark Office in connection with U.S. Appl. No. 13/708,525, dated Feb. 3, 2016, 23 pages.

(56) References Cited

OTHER PUBLICATIONS

Examiner's Answer, issued by the United States Patent and Trademark Office in connection with U.S. Appl. No. 13/730,511, dated Feb. 18, 2016, 5 pages.
Non-Final Office Action, issued by the United States Patent and Trademark Office in connection with U.S. Appl. No. 12/410,372, dated Feb. 23, 2016, 24 pages.
English Translation of Notification of Provisional Rejection, issued by the Korean Patent Office in connection with Patent Application No. 10-2010-7001406, dated Jan. 26, 2016, 1 page.
English Translation of Notification to Grant Patent Right for Invention, issued by the State Intellectual Property Office of P.R. China in connection with Patent Application No. 200880017883.X, dated Feb. 3, 2016, 2 pages.
Landau et al., "Different Effects of Voluntary and Involunatry Attention on EEG Activity in the Gamma Band," J of Neuroscience 27(44), Oct. 31, 2007, pp. 11986-11990, 5 pages.
Final Office Action, issued by the United States Patent and Trademark Office in connection with U.S. Appl. No. 14/177,698, dated Apr. 24, 2015, 13 pages.
Final Office Action, issued by the United States Patent and Trademark Office in connection with U.S. Appl. No. 12/608,685, dated May 5, 2015, 7 pages.
Final Office Action, issued by the United States Patent and Trademark Office in connection with U.S. Appl. No. 13/730,511, dated May 6, 2015, 5 pages.
Final Office Action, issued by the United States Patent and Trademark Office in connection with U.S. Appl. No. 13/105,774, dated May 14, 2015, 15 pages.
Final Office Action, issued by the United States Patent and Trademark Office in connection with U.S. Appl. No. 12/884,034, dated May 14, 2015, 22 pages.
Final Office Action, issued by the United States Patent and Trademark Office in connection with U.S. Appl. No. 13/730,564, dated May 22, 2015, 6 pages.
Final Office Action, issued by the United States Patent and Trademark Office in connection with U.S. Appl. No. 13/249,512, dated Jun. 30, 2015, 36 pages.
English Translation of Office Action, issued by the Israeli Patent Office in connection with Patent Application No. 201187, dated Jun. 22, 2015, 4 pages.
Notification of Provisional Rejection, issued by the Korean Patent Office in connection with Patent Application No. 10-2010-7001406, dated Jun. 24, 2015 (with partial translation), 9 pages.
McClure, Samuel, et al., "Neural Correlates of Behavioral Preference for Culturally Familiar Drinks," Neuron (Oct. 14, 2004), 379-387, 9 pages.

Final Office Action, issued by the United States Patent and Trademark Office in connection with U.S. Appl. No. 13/730,541, dated Feb. 12, 2015, 6 pages.
Non-Final Office Action, issued by the United States Patent and Trademark Office in connection with U.S. Appl. No. 13/730,550, dated Feb. 20, 2015, 5 pages.
Final Office Action, issued by the United States Patent and Trademark Office in connection with U.S. Appl. No. 12/608,660, dated Feb. 20, 2015, 18 pages.
Final Office Action, issued by the United States Patent and Trademark Office in connection with U.S. Appl. No. 13/965,805, dated Mar. 6, 2015, 18 pages.
Non-Final Office Action, issued by the United States Patent and Trademark Office in connection with U.S. Appl. No. 13/708,344, dated Apr. 9, 2015, 12 pages.
Final Office Action, issued by the United States Patent and Trademark Office in connection with U.S. Appl. No. 12/884,034, dated May 3, 2018, 46 pages.
Non-Final Office Action, issued by the United States Patent and Trademark Office in connection with U.S. Appl. No. 13/708,525, dated May 18, 2018, 31 pages.
Communication Under Rule 71(3) EPC, issued by the European Patent Office in connection with European Application No. 08796890.5, dated Mar. 16, 2018, 43 pages.
English Translation of First Examination Report, issued by the Indian Patent Office in connection with Indian Patent Application No. 4441/KOLNP/2009, dated May 21, 2018, 5 pages.
Decision on Appeal, issued by the United States Patent and Trademark Office in connection with U.S. Appl. No. 13/730,564, on Feb. 2, 2018, 10 pages.
Decision on Appeal, issued by the United States Patent and Trademark Office in connection with U.S. Appl. No. 13/730,511, on Mar. 1, 2018, 14 pages.
Decision on Appeal, issued by the United States Patent and Trademark Office in connection with U.S. Appl. No. 13/730,550, on Mar. 27, 2018, 13 pages.
Notice of Allowance, issued by the United States Patent and Trademark Office in connection with U.S. Appl. No. 15/299,752, dated Apr. 17, 2018, 21 pages.
Final Office Action, issued by the United States Patent and Trademark Office in connection with U.S. Appl. No. 12/546,586, dated Jun. 28, 2018, 22 pages.
Decision on Request for Rehearing, issued by the United States Patent and Trademark Office in connection with U.S. Appl. No. 12/608,685, dated Aug. 10, 2018, 8 pages.
Decision on Appeal, issued by the United States Patent and Trademark Office in connection with U.S. Appl. No. 13/965,805, dated Sep. 10, 2018, 11 pages.
Decision on Appeal, issued by the United States Patent and Trademark Office in connection with U.S. Appl. No. 12/234,372, dated Sep. 19, 2018, 8 pages.

| Stimulus Attributes Data Model 201 | | | | |
|---|---|---|---|---|
| Channel 203 | Media 205 | Time Span 207 | Audience 209 | Demography 211 | ... |

| Stimulus Purpose Data Model 215 | | |
|---|---|---|
| Intent 217 | Objectives 219 | Candidate Location Information 221 | ... |

| Stimulus Attributes Data Model 221 | | | |
|---|---|---|---|
| Creation Attributes 223 | Ownership Attributes 225 | Broadcast Attributes 227 | Statistical, Demographic, And Survey Based Identifiers 229 |

Figure 2

Dataset Data Model 301

| Experiment Name 303 | Client Attributes 305 | Subject Pool 307 | Logistics Information 309 | Stimulus Material 311 | ... |

Subject Attributes Data Model 315

| Subject Name 317 | Demographic Attributes 319 | Contact Information 321 | ... |

Neuro-Feedback Association Data Model 325

| Experiment Protocols 327 | Modalities included 329 | Experiment Design Parameters 333 | ... |

Data Collection Data Model 337

| Recording Attributes 339 | Equipment Attributes 341 | Modalities Recorded 343 | Data Storage Attributes 345 | ... |

Preset Query Data Model 349

| Query Name 351 | Accessed Data Collection 353 | Access Security Attributes 355 | Refresh Attributes 357 | ... |

Figure 3

| Subject Attributes Queries 415 | |
|---|---|
| Location 417 | Demographic Attributes 419 | Session Information 421 | ... |

| Experimental Design Queries 425 | |
|---|---|
| Experiment Protocols 427 | Product Category 429 | Surveys Included 431 | Stimulus Used 433 | ... |

| Response Assessment Queries 437 | |
|---|---|
| Attention Score 439 | Emotion Score 441 | Retention Score 443 | Effectiveness Score 445 | ... |

Figure 4

| Client Assessment Summary Reports 501 | |
|---|---|
| Effectiveness 503 | Component Assessment 505 | Resonance Measures 507 | ... |

| Client Cumulative Reports 511 | | |
|---|---|---|
| Media Grouped 513 | Campaign Grouped 515 | Time/Location Grouped 517 | ... |

| Industry Cumulative And Syndicated Reports 521 | | | |
|---|---|---|---|
| Aggregate Assessment 523 | Top Performers 525 | Bottom Performers 527 | Outliers 529 | Trend 531 |

Figure 5

STIMULUS PLACEMENT SYSTEM USING SUBJECT NEURO-RESPONSE MEASUREMENTS

CROSS-REFERENCE TO RELATED APPLICATIONS

This patent arises from a continuation of U.S. patent application Ser. No. 12/199,557, which was filed on Aug. 27, 2008, and issued as U.S. Pat. No. 8,386,313, and claims the benefit under 35 U.S.C. § 119(e) of U.S. Patent Provisional Application Ser. No. 60/968,558, which was filed on Aug. 28, 2007, both of which are hereby incorporated herein by reference in their entireties.

FIELD OF THE DISCLOSURE

The present disclosure relates to placing stimulus material using subject neuro-response measurements.

BACKGROUND

Conventional systems for placing stimulus material such as a media clip, product, brand image, offering, etc., are limited. Some placement systems are based on demographic information, statistical data, and survey based response collection. However, conventional systems are subject to semantic, syntactic, metaphorical, cultural, and interpretive errors.

BRIEF DESCRIPTION OF THE DRAWINGS

The disclosure may best be understood by reference to the following description taken in conjunction with the accompanying drawings, which illustrate particular examples.

FIG. 2 illustrates examples of stimulus attributes that can be included in a stimulus attributes repository.

FIG. 3 illustrates examples of data models that can be used with a stimulus and response repository.

FIG. 4 illustrates one example of a query that can be used with a stimulus location selection system.

FIG. 5 illustrates one example of a report generated using the stimulus location selection system.

DETAILED DESCRIPTION

Figure 1:
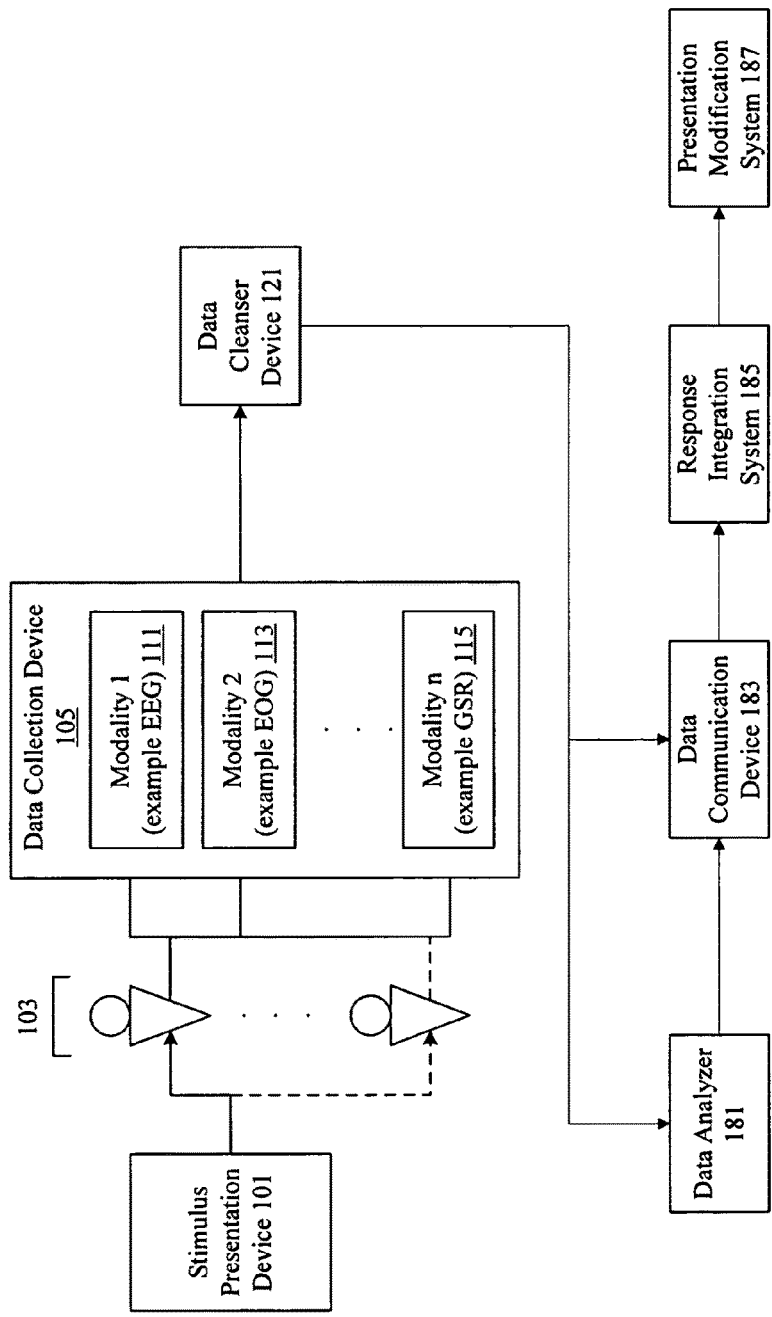
FIG. 1 illustrates one example of a system for selecting locations for stimulus material introduction.

Reference will now be made in detail to some specific examples of the disclosure including the best modes contemplated by the inventors for carrying out the teachings of the disclosure. Examples of these specific examples are illustrated in the accompanying drawings. While the disclosure is described in conjunction with these specific examples, it will be understood that it is not intended to limit the disclosure to the described examples. On the contrary, it is intended to cover alternatives, modifications, and equivalents as may be included within the spirit and scope of the disclosure as defined by the appended claims.

For example, the techniques and mechanisms of the present disclosure will be described in the context of particular types of data such as central nervous system, autonomic nervous system, and effector data. However, it should be noted that the techniques and mechanisms of the present disclosure apply to a variety of different types of data. It should be noted that various mechanisms and techniques can be applied to any type of stimuli. In the following description, numerous specific details are set forth in order to provide a thorough understanding of the present disclosure. Particular examples of the present disclosure may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some examples include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Overview

Consequently, it is desirable to provide improved methods and apparatus for selecting locations for introduction of stimulus materials.

A system evaluates and selects temporal and spatial locations for introduction of stimulus material. Video streams, physical locations, print advertisements, store shelves, images, commercials, etc. are analyzed to identify locations for introducing stimulus material, such as messages, brand images, products, media, marketing and/or other sales materials. The system analyzes neuro-response measurements from subjects exposed to stimulus material in different temporal and spatial locations. Examples of neuro-response measurements include Electroencephalography (EEG), Galvanic Skin Response (GSR), Electrocardiograms (EKG), Electrooculography (EOG), eye tracking, and facial emotion encoding measurements. Neuro-response measurements are analyzed to select temporal and spatial locations for introduction of stimulus material.

EXAMPLES

Conventional placement systems such as product placement systems often rely on demographic information, statistical information, and survey based response collection to determine optimal locations to place stimulus material, such as a new product, a brand image, a video clip, sound files, etc. One problem with conventional stimulus placement systems is that conventional stimulus placement systems do not accurately measure the responses to components of the experience. They are also prone to semantic, syntactic, metaphorical, cultural, and interpretive errors thereby preventing the accurate and repeatable selection of stimulus placement locations.

Conventional systems do not use neuro-behavioral and neuro-physiological response blended manifestations in assessing the user response and do not elicit an individual customized neuro-physiological and/or neuro-behavioral response to the stimulus.

Conventional devices also fail to blend multiple datasets, and blended manifestations of multi-modal responses, across multiple datasets, individuals and modalities, to reveal and validate stimulus location selection.

In these respects, the neuro-physiological and neuro-behavioral stimulus location selection system according to the present disclosure substantially departs from the conventional concepts and designs of the prior art, and in so doing provides an apparatus developed to provide neuro-physiological and neuro-behavioral response based measurements to select stimulus locations. The selection mechanism may include marketing, advertising and other audio/visual/tactile/olfactory stimulus including but not limited to communication, concept, experience, message, images, audio, pricing, and packaging.

The techniques and mechanisms of the present disclosure use neuro-response measurements such as central nervous system, autonomic nervous system, and effector measurements to improve stimulus location selection. Some examples of central nervous system measurement mechanisms include Functional Magnetic Resonance Imaging (FMRI) and Electroencephalography (EEG). fMRI measures blood oxygenation in the brain that correlates with increased neural activity. However, current implementations of fMRI have poor temporal resolution of few seconds. EEG measures electrical activity associated with post synaptic currents occurring in the milliseconds range. Subcranial EEG can measure electrical activity with the most accuracy, as the bone and dermal layers weaken transmission of a wide range of frequencies. Nonetheless, surface EEG provides a wealth of electrophysiological information if analyzed properly. Even portable EEG with dry electrodes provide a large amount of neuro-response information.

Autonomic nervous system measurement mechanisms include Galvanic Skin Response (GSR), Electrocardiograms (EKG), pupillary dilation, etc. Effector measurement mechanisms include Electrooculography (EOG), eye tracking, facial emotion encoding, reaction time etc.

According to various examples, the techniques and mechanisms of the present disclosure intelligently blend multiple modes and manifestations of precognitive neural signatures with cognitive neural signatures and post cognitive neurophysiological manifestations to more accurately perform stimulus location selection. In some examples, autonomic nervous system measures are themselves used to validate central nervous system measures. Effector and behavior responses are blended and combined with other measures. According to various examples, central nervous system, autonomic nervous system, and effector system measurements are aggregated into a measurement that allows assessment of the effectiveness of the source material with stimulus material introduced at various locations.

In particular examples, subjects are exposed to stimulus material and data such as central nervous system, autonomic nervous system, and effector data is collected during exposure. According to various examples, data is collected in order to assess neuro-response significance for source material with stimulus material introduced at various temporal and spatial locations. For example, a billboard may be evaluated for neuro-response significance before introducing any additional stimulus material. Areas of the billboard having low neuro-response significance are then identified as candidate locations for introducing stimulus material. Stimulus material such as a brand image is then introduced onto various versions the billboard at candidate temporal and spatial locations and neuro-response significance for each of the versions is evaluated. In other examples, lulls in neuro-response significance are identified as candidate locations. In still other examples, still screens in a video or blank portions of an image are identified as candidate locations. Candidate locations may also be manually identified.

Many types of stimulus material may be placed into source material. In some examples, source material is a physical display and stimulus material is a newly packaged product for the display. In other examples, brand images are introduced into a video. Text advertisements may be placed onto a web page or audio clips may be added to a music file. Any type of stimulus material may be added to source material.

In particular examples, specific event related potential (ERP) analyses and/or event related power spectral perturbations (ERPSPs) are evaluated for different regions of the brain both before a subject is exposed to stimulus and each time after the subject is exposed to stimulus.

Pre-stimulus and post-stimulus differential as well as target and distracter differential measurements of ERP time domain components at multiple regions of the brain are determined (DERP). Event related time-frequency analysis of the differential response to assess the attention, emotion and memory retention (DERPSPs) across multiple frequency bands including but not limited to theta, alpha, beta, gamma and high gamma is performed. In particular examples, single trial and/or averaged DERP and/or DERPSPs can be used to enhance selection of stimulus locations.

A stimulus placement mechanism may incorporate relationship assessments using brain regional coherence measures of segments of the stimuli relevant to the entity/relationship, segment effectiveness measures synthesizing the attention, emotional engagement and memory retention estimates based on the neuro-physiological measures including time-frequency analysis of EEG measurements, and differential saccade related neural signatures during segments where coupling/relationship patterns are emerging in comparison to segments with non-coupled interactions.

According to various examples, a stimulus location selection system can include automated systems with or without human intervention for the elicitation of potential object/individual groupings. For example, these could also include pattern recognition and object identification techniques. These sub-systems could include a hardware implementation and/or software implementations.

A variety of stimulus materials such as entertainment and marketing materials, media streams, billboards, print advertisements, text streams, music, performances, sensory experiences, etc., can be analyzed. According to various examples, enhanced neuro-response data is generated using a data analyzer that performs both intra-modality measurement enhancements and cross-modality measurement enhancements. According to various examples, brain activity is measured not just to determine the regions of activity, but to determine interactions and types of interactions between various regions. The techniques and mechanisms of the present disclosure recognize that interactions between neural regions support orchestrated and organized behavior. Attention, emotion, memory, and other abilities are not merely based on one part of the brain but instead rely on network interactions between brain regions.

The techniques and mechanisms of the present disclosure further recognize that different frequency bands used for multi-regional communication can be indicative of the effectiveness of stimuli. In particular examples, evaluations are calibrated to each subject and synchronized across subjects. In particular examples, templates are created for subjects to create a baseline for measuring pre and post stimulus differentials. According to various examples, stimulus generators are intelligent and adaptively modify specific parameters such as exposure length and duration for each subject being analyzed.

A variety of modalities can be used including EEG, GSR, EKG, pupillary dilation, EOG, eye tracking, facial emotion encoding, reaction time, etc. Individual modalities such as EEG are enhanced by intelligently recognizing neural region communication pathways. Cross modality analysis is enhanced using a synthesis and analytical blending of central nervous system, autonomic nervous system, and effector signatures. Synthesis and analysis by mechanisms such as time and phase shifting, correlating, and validating intra-modal determinations allow generation of a composite output characterizing the significance of various data responses to effectively perform stimulus location selection.

FIG. 1 illustrates one example of a system for performing stimulus placement or stimulus location selection using central nervous system, autonomic nervous system, and/or effector measures. According to various examples, the stimulus location selection system includes a stimulus presentation device 101. In particular examples, the stimulus presentation device 101 is merely a display, monitor, screen, etc., that displays stimulus material to a user. The stimulus material may be a media clip, a commercial, pages of text, a brand image, a performance, a magazine advertisement, a movie, an experience, an audio presentation, and may even involve particular tastes, smells, textures and/or sounds. The stimuli can involve a variety of senses and occur with or without human supervision. In other examples, stimulus presentation may involve providing the user with a product, service, offering, or experience. Continuous and discrete modes are supported. According to various examples, the stimulus presentation device 101 also has protocol generation capability to allow intelligent customization of stimuli provided to multiple subjects in different markets.

According to various examples, stimulus presentation device 101 could include devices such as televisions, cable consoles, computers and monitors, projection systems, display devices, speakers, tactile surfaces, etc., for presenting the stimuli including but not limited to advertising and entertainment from different networks, local networks, cable channels, syndicated sources, websites, internet content aggregators, portals, service providers, etc.

According to various examples, the subjects are connected to data collection devices 105. The data collection devices 105 may include a variety of neuro-response measurement mechanisms including neurological and neuro-physiological measurements systems such as EEG, EOG, GSR, EKG, pupillary dilation, eye tracking, facial emotion encoding, and reaction time devices, etc. According to various examples, neuro-response data includes central nervous system, autonomic nervous system, and effector data. In particular examples, the data collection devices 105 include EEG 111, EOG 113, and GSR 115. In some instances, only a single data collection device is used. Data collection may proceed with or without human supervision.

The data collection device 105 collects neuro-response data from multiple sources. This includes a combination of devices such as central nervous system sources (EEG), autonomic nervous system sources (GSR, EKG, pupillary dilation), and effector sources (EOG, eye tracking, facial emotion encoding, reaction time). In particular examples, data collected is digitally sampled and stored for later analysis. In particular examples, the data collected could be analyzed in real-time. According to particular examples, the digital sampling rates are adaptively chosen based on the neurophysiological and neurological data being measured.

In one particular example, the stimulus location selection system includes EEG 111 measurements made using scalp level electrodes, EOG 113 measurements made using shielded electrodes to track eye data, GSR 115 measurements performed using a differential measurement system, a facial muscular measurement through shielded electrodes placed at specific locations on the face, and a facial affect graphic and video analyzer adaptively derived for each individual.

In particular examples, the data collection devices are clock synchronized with a stimulus presentation device 101. In particular examples, the data collection devices 105 also include a condition evaluation subsystem that provides auto triggers, alerts and status monitoring and visualization components that continuously monitor the status of the subject, data being collected, and the data collection instruments. The condition evaluation subsystem may also present visual alerts and automatically trigger remedial actions. According to various examples, the data collection devices include mechanisms for not only monitoring subject neuro-response to stimulus materials, but also include mechanisms for identifying and monitoring the stimulus materials. For example, data collection devices 105 may be synchronized with a set-top box to monitor channel changes. In other examples, data collection devices 105 may be directionally synchronized to monitor when a subject is no longer paying attention to stimulus material. In still other examples, the data collection devices 105 may receive and store stimulus material generally being viewed by the subject, whether the stimulus is a program, a commercial, printed material, an experience, or a scene outside a window. The data collected allows analysis of neuro-response information and correlation of the information to actual stimulus material and not mere subject distractions.

According to various examples, the stimulus location selection system also includes a data cleanser device 121. In particular examples, the data cleanser device 121 filters the collected data to remove noise, artifacts, and other irrelevant data using fixed and adaptive filtering, weighted averaging, advanced component extraction (like PCA, ICA), vector and component separation methods, etc. This device cleanses the data by removing both exogenous noise (where the source is outside the physiology of the subject, e.g. a phone ringing while a subject is viewing a video) and endogenous artifacts (where the source could be neurophysiological, e.g. muscle movements, eye blinks, etc.).

The artifact removal subsystem includes mechanisms to selectively isolate and review the response data and identify epochs with time domain and/or frequency domain attributes that correspond to artifacts such as line frequency, eye blinks, and muscle movements. The artifact removal subsystem then cleanses the artifacts by either omitting these epochs, or by replacing these epoch data with an estimate based on the other clean data (for example, an EEG nearest neighbor weighted averaging approach).

According to various examples, the data cleanser device 121 is implemented using hardware, firmware, and/or software. It should be noted that although a data cleanser device 121 is shown located after a data collection device 105 and before data analyzer 181, the data cleanser device 121 like other components may have a location and functionality that varies based on system implementation. For example, some systems may not use any automated data cleanser device whatsoever while in other systems, data cleanser devices may be integrated into individual data collection devices.

According to various examples, an optional stimulus attributes repository 131 provides information on the stimulus material being presented to the multiple subjects. According to various examples, stimulus attributes include properties of the stimulus materials as well as purposes, presentation attributes, report generation attributes, etc. In particular examples, stimulus attributes include time span, channel, rating, media, type, etc. Stimulus attributes may also include positions of entities in various frames, components, events, object relationships, locations of objects and duration of display. Purpose attributes include aspiration and objects of the stimulus including excitement, memory retention, associations, etc. Presentation attributes include audio, video, imagery, and messages needed for enhancement or avoidance. Other attributes may or may not also be included in the stimulus attributes repository or some other repository.

The data cleanser device 121 and the stimulus attributes repository 131 pass data to the data analyzer 181. The data analyzer 181 uses a variety of mechanisms to analyze underlying data in the system to place stimulus. According to various examples, the data analyzer customizes and extracts the independent neurological and neuro-physiological parameters for each individual in each modality, and blends the estimates within a modality as well as across modalities to elicit an enhanced response to the presented stimulus material. In particular examples, the data analyzer 181 aggregates the response measures across subjects in a dataset.

According to various examples, neurological and neuro-physiological signatures are measured using time domain analyses and frequency domain analyses. Such analyses use parameters that are common across individuals as well as parameters that are unique to each individual. The analyses could also include statistical parameter extraction and fuzzy logic based attribute estimation from both the time and frequency components of the synthesized response.

In some examples, statistical parameters used in a blended effectiveness estimate include evaluations of skew, peaks, first and second moments, population distribution, as well as fuzzy estimates of attention, emotional engagement and memory retention responses.

According to various examples, the data analyzer 181 may include an intra-modality response synthesizer and a cross-modality response synthesizer. In particular examples, the intra-modality response synthesizer is configured to customize and extract the independent neurological and neurophysiological parameters for each individual in each modality and blend the estimates within a modality analytically to elicit an enhanced response to the presented stimuli. In particular examples, the intra-modality response synthesizer also aggregates data from different subjects in a dataset.

According to various examples, the cross-modality response synthesizer or fusion device blends different intra-modality responses, including raw signals and signals output. The combination of signals enhances the measures of effectiveness within a modality. The cross-modality response fusion device can also aggregate data from different subjects in a dataset.

According to various examples, the data analyzer 181 also includes a composite enhanced effectiveness estimator (CEEE) that combines the enhanced responses and estimates from each modality to provide a blended estimate of the effectiveness. In particular examples, blended estimates are provided for each exposure of a subject to stimulus materials. The blended estimates are evaluated over time to assess stimulus location characteristics. According to various examples, numerical values are assigned to each blended estimate. The numerical values may correspond to the intensity of neuro-response measurements, the significance of peaks, the change between peaks, etc. Higher numerical values may correspond to higher significance in neuro-response intensity. Lower numerical values may correspond to lower significance or even insignificant neuro-response activity. In other examples, multiple values are assigned to each blended estimate. In still other examples, blended estimates of neuro-response significance are graphically represented to show changes after repeated exposure.

According to various examples, the data analyzer 181 provides analyzed and enhanced response data to a data communication device 183. It should be noted that in particular instances, a data communication device 183 is not necessary. According to various examples, the data communication device 183 provides raw and/or analyzed data and insights. In particular examples, the data communication device 183 may include mechanisms for the compression and encryption of data for secure storage and communication.

According to various examples, the data communication device 183 transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, the data communication device is a set top box, wireless device, computer system, etc. that transmits data obtained from a data collection device to a response integration system 185. In particular examples, the data communication device may transmit data even before data cleansing or data analysis. In other examples, the data communication device may transmit data after data cleansing and analysis.

In particular examples, the data communication device 183 sends data to a response integration system 185. According to various examples, the response integration system 185 assesses and extracts stimulus placement characteristics. In particular examples, the response integration system 185 determines entity positions in various stimulus segments and matches position information with eye tracking paths while correlating saccades with neural assessments of attention, memory retention, and emotional engagement. In particular examples, the response integration system 185 also collects and integrates user behavioral and survey responses with the analyzed response data to more effectively select stimulus locations.

A variety of data can be stored for later analysis, management, manipulation, and retrieval. In particular examples, the repository could be used for tracking stimulus attributes and presentation attributes, audience responses and optionally could also be used to integrate audience measurement information.

As with a variety of the components in the system, the response integration system can be co-located with the rest of the system and the user, or could be implemented in a remote location. It could also be optionally separated into an assessment repository system that could be centralized or distributed at the provider or providers of the stimulus material. In other examples, the response integration system is housed at the facilities of a third party service provider accessible by stimulus material providers and/or users.

FIG. 2 illustrates examples of data models that may be provided with a stimulus attributes repository. According to various examples, a stimulus attributes data model 201 includes a channel 203, media type 205, time span 207, audience 209, and demographic information 211. A stimulus purpose data model 215 may include intents 217 and objectives 219. According to various examples, stimulus attributes data model 201 also includes candidate location information 221 about various temporal, spatial, activity, and event components in an experience that may hold stimulus material. For example, a movie may show a blank wall included on some scenes that can be used to display an advertisement. The temporal and spatial characteristics of the blank wall may be provided in candidate location information 221.

According to various examples, another stimulus attributes data model includes creation attributes 223, ownership attributes 225, broadcast attributes 227, and statistical, demographic and/or survey based identifiers for automatically integrating the neuro-physiological and neuro-behavioral response with other attributes and meta-information associated with the stimulus.

FIG. 3 illustrates examples of data models that can be used for storage of information associated with selection of locations for the introduction of stimulus material. According to various examples, a dataset data model 301 includes an experiment name 303 and/or identifier, client attributes 305, a subject pool 307, logistics information 309 such as the location, date, and time of testing, and stimulus material 311 including stimulus material attributes.

In particular examples, a subject attribute data model 315 includes a subject name 317 and/or identifier, contact information 321, and demographic attributes 319 that may be useful for review of neurological and neuro-physiological data. Some examples of pertinent demographic attributes include marriage status, employment status, occupation, household income, household size and composition, ethnicity, geographic location, sex, race. Other fields that may be included in data model 315 include shopping preferences, entertainment preferences, and financial preferences. Shopping preferences include favorite stores, shopping frequency, categories shopped, favorite brands. Entertainment preferences include network/cable/satellite access capabilities, favorite shows, favorite genres, and favorite actors. Financial preferences include favorite insurance companies, preferred investment practices, banking preferences, and favorite online financial instruments. A variety of subject attributes may be included in a subject attributes data model 315 and data models may be preset or custom generated to suit particular purposes.

According to various examples, data models for neuro-feedback association 325 identify experimental protocols 327, modalities included 329 such as EEG, EOG, GSR, surveys conducted, and experiment design parameters 333 such as segments and segment attributes. Other fields may include experiment presentation scripts, segment length, segment details like stimulus material used, inter-subject variations, intra-subject variations, instructions, presentation order, survey questions used, etc. Other data models may include a data collection data model 337. According to various examples, the data collection data model 337 includes recording attributes 339 such as station and location identifiers, the data and time of recording, and operator details. In particular examples, equipment attributes 341 include an amplifier identifier and a sensor identifier.

Modalities recorded 343 may include modality specific attributes like EEG cap layout, active channels, sampling frequency, and filters used. EOG specific attributes include the number and type of sensors used, location of sensors applied, etc. Eye tracking specific attributes include the type of tracker used, data recording frequency, data being recorded, recording format, etc. According to various examples, data storage attributes 345 include file storage conventions (format, naming convention, dating convention), storage location, archival attributes, expiry attributes, etc.

A preset query data model 349 includes a query name 351 and/or identifier, an accessed data collection 353 such as data segments involved (models, databases/cubes, tables, etc.), access security attributes 355 included who has what type of access, and refresh attributes 357 such as the expiry of the query, refresh frequency, etc. Other fields such as push-pull preferences can also be included to identify an auto push reporting driver or a user driven report retrieval system.

FIG. 4 illustrates examples of queries that can be performed to obtain data associated with stimulus location selection. For example, users may query to determine what types of consumers respond most to a particular experience or component of an experience. According to various examples, queries are defined from general or customized scripting languages and constructs, visual mechanisms, a library of preset queries, diagnostic querying including drill-down diagnostics, and eliciting what if scenarios. According to various examples, subject attributes queries 415 may be configured to obtain data from a neuro-informatics repository using a location 417 or geographic information, session information 421 such as testing times and dates, and demographic attributes 419. Demographics attributes include household income, household size and status, education level, age of kids, etc.

Other queries may retrieve stimulus material based on shopping preferences of subject participants, countenance, physiological assessment, completion status. For example, a user may query for data associated with product categories, products shopped, shops frequented, subject eye correction status, color blindness, subject state, signal strength of measured responses, alpha frequency band ringers, muscle movement assessments, segments completed, etc. Experimental design based queries may obtain data from a neuro-informatics repository based on experiment protocols 427, product category 429, surveys included 431, and stimulus provided 433. Other fields that may be used include the number of protocol repetitions used, combination of protocols used, and usage configuration of surveys.

Client and industry based queries may obtain data based on the types of industries included in testing, specific categories tested, client companies involved, and brands being tested. Response assessment based queries 437 may include attention scores 439, emotion scores, 441, retention scores 443, and effectiveness scores 445. Such queries may obtain materials that elicited particular scores.

Response measure profile based queries may use mean measure thresholds, variance measures, number of peaks detected, etc. Group response queries may include group statistics like mean, variance, kurtosis, p-value, etc., group size, and outlier assessment measures. Still other queries may involve testing attributes like test location, time period, test repetition count, test station, and test operator fields. A variety of types and combinations of types of queries can be used to efficiently extract data.

FIG. 5 illustrates examples of reports that can be generated. According to various examples, client assessment summary reports 501 include effectiveness measures 503, component assessment measures 505, and stimulus location effectiveness measures 507. Effectiveness assessment measures include composite assessment measure(s), industry/category/client specific placement (percentile, ranking, etc.), actionable grouping assessment such as removing material, modifying segments, or fine tuning specific elements, etc, and the evolution of the effectiveness profile over time. In particular examples, component assessment reports include component assessment measures like attention, emotional engagement scores, percentile placement, ranking, etc. Component profile measures include time based evolution of the component measures and profile statistical assessments. According to various examples, reports include the number of times material is assessed, attributes of the multiple presentations used, evolution of the response assessment measures over the multiple presentations, and usage recommendations.

According to various examples, client cumulative reports 511 include media grouped reporting 513 of all stimulus assessed, campaign grouped reporting 515 of stimulus assessed, and time/location grouped reporting 517 of stimulus assessed. According to various examples, industry cumulative and syndicated reports 521 include aggregate assessment responses measures 523, top performer lists 525, bottom performer lists 527, outliers 529, and trend reporting 531. In particular examples, tracking and reporting includes specific products, categories, companies, brands.

Figure 6:
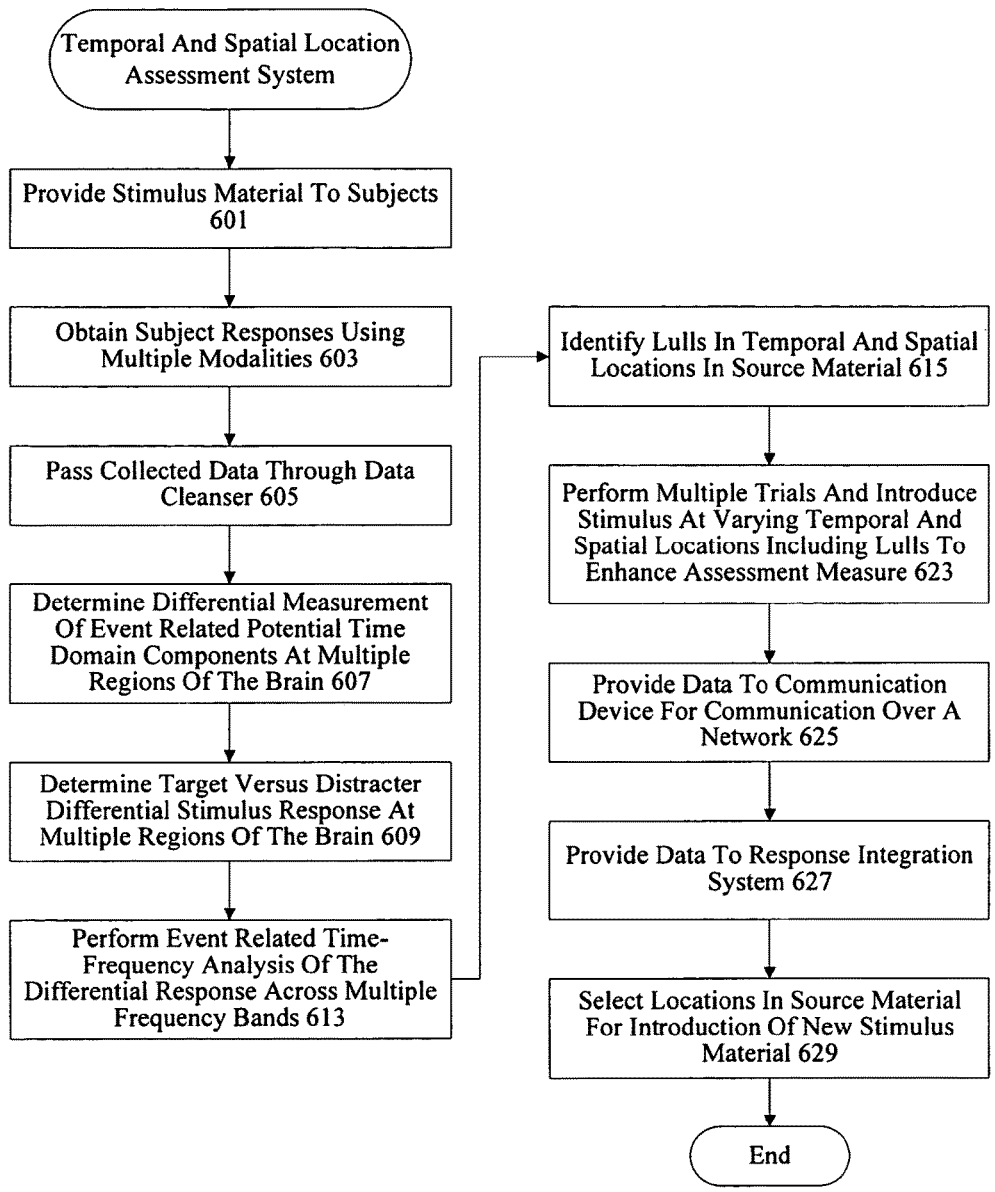
FIG. 6 illustrates one example of a technique for performing temporal and spatial location assessment.

FIG. 6 illustrates one example of stimulus location selection. At 601, stimulus material is provided to multiple subjects in multiple geographic markets. According to various examples, stimulus includes streaming video and audio provided over mechanisms such as broadcast television, cable television, satellite, etc. Alternatively, stimulus may involve actual physical products, services, interactions, and experiences. At 603, subject responses are collected using a variety of modalities, such as EEG, ERP, EOG, GSR, etc. In some examples, verbal and written responses can also be collected and correlated with neurological and neurophysiological responses. At 605, data is passed through a data cleanser to remove noise and artifacts that may make data more difficult to interpret. According to various examples, the data cleanser removes EEG electrical activity associated with blinking and other endogenous/exogenous artifacts.

According to various examples, data analysis is performed. Data analysis may include intra-modality response synthesis and cross-modality response synthesis to enhance effectiveness measures. It should be noted that in some particular instances, one type of synthesis may be performed without performing other types of synthesis. For example, cross-modality response synthesis may be performed with or without intra-modality synthesis.

A variety of mechanisms can be used to perform data analysis. In particular examples, a stimulus attributes repository is accessed to obtain attributes and characteristics of the stimulus materials, along with purposes, intents, objectives, etc. In particular examples, EEG response data is synthesized to provide an enhanced assessment of effectiveness. According to various examples, EEG measures electrical activity resulting from thousands of simultaneous neural processes associated with different portions of the brain. EEG data can be classified in various bands. According to various examples, brainwave frequencies include delta, theta, alpha, beta, and gamma frequency ranges. Delta waves are classified as those less than 4 Hz and are prominent during deep sleep. Theta waves have frequencies between 3.5 to 7.5 Hz and are associated with memories, attention, emotions, and sensations. Theta waves are typically prominent during states of internal focus.

Alpha frequencies reside between 7.5 and 13 Hz and typically peak around 10 Hz. Alpha waves are prominent during states of relaxation. Beta waves have a frequency range between 14 and 30 Hz. Beta waves are prominent during states of motor control, long range synchronization between brain areas, analytical problem solving, judgment, and decision making. Gamma waves occur between 30 and 60 Hz and are involved in binding of different populations of neurons together into a network for the purpose of carrying out a certain cognitive or motor function, as well as in attention and memory. Because the skull and dermal layers attenuate waves in this frequency range, brain waves above 75-80 Hz are difficult to detect and are often not used for stimuli response assessment.

However, the techniques and mechanisms of the present disclosure recognize that analyzing high gamma band (kappa-band: Above 60 Hz) measurements, in addition to theta, alpha, beta, and low gamma band measurements, enhances neurological attention, emotional engagement and retention component estimates. In particular examples, EEG measurements including difficult to detect high gamma or kappa band measurements are obtained, enhanced, and evaluated. Subject and task specific signature sub-bands in the theta, alpha, beta, gamma and kappa bands are identified to provide enhanced response estimates. According to various examples, high gamma waves (kappa-band) above 80 Hz (typically detectable with sub-cranial EEG and/or magnetoencephalography) can be used in inverse model-based enhancement of the frequency responses to the stimuli.

Various examples of the present disclosure recognize that particular sub-bands within each frequency range have particular prominence during certain activities. A subset of the frequencies in a particular band is referred to herein as a sub-band. For example, a sub-band may include the 40-45 Hz range within the gamma band. In particular examples, multiple sub-bands within the different bands are selected while remaining frequencies are band pass filtered. In particular examples, multiple sub-band responses may be enhanced, while the remaining frequency responses may be attenuated.

An information theory based band-weighting model is used for adaptive extraction of selective dataset specific, subject specific, task specific bands to enhance the effectiveness measure. Adaptive extraction may be performed using fuzzy scaling. Stimuli can be presented and enhanced measurements determined multiple times to determine the variation profiles across multiple presentations. Determining various profiles provides an enhanced assessment of the primary responses as well as the longevity (wear-out) of the marketing and entertainment stimuli. The synchronous response of multiple individuals to stimuli presented in concert is measured to determine an enhanced across subject synchrony measure of effectiveness. According to various examples, the synchronous response may be determined for multiple subjects residing in separate locations or for multiple subjects residing in the same location.

Although a variety of synthesis mechanisms are described, it should be recognized that any number of mechanisms can be applied—in sequence or in parallel with or without interaction between the mechanisms.

Although intra-modality synthesis mechanisms provide enhanced significance data, additional cross-modality synthesis mechanisms can also be applied. A variety of mechanisms such as EEG, Eye Tracking, GSR, EOG, and facial emotion encoding are connected to a cross-modality synthesis mechanism. Other mechanisms as well as variations and enhancements on existing mechanisms may also be included. According to various examples, data from a specific modality can be enhanced using data from one or more other modalities. In particular examples, EEG typically makes frequency measurements in different bands like alpha, beta and gamma to provide estimates of significance. However, the techniques of the present disclosure recognize that significance measures can be enhanced further using information from other modalities.

For example, facial emotion encoding measures can be used to enhance the valence of the EEG emotional engagement measure. EOG and eye tracking saccadic measures of object entities can be used to enhance the EEG estimates of significance including but not limited to attention, emotional engagement, and memory retention. According to various examples, a cross-modality synthesis mechanism performs time and phase shifting of data to allow data from different modalities to align. In some examples, it is recognized that an EEG response will often occur hundreds of milliseconds before a facial emotion measurement changes. Correlations can be drawn and time and phase shifts made on an individual as well as a group basis. In other examples, saccadic eye movements may be determined as occurring before and after particular EEG responses. According to various examples, time corrected GSR measures are used to scale and enhance the EEG estimates of significance including attention, emotional engagement and memory retention measures.

Evidence of the occurrence or non-occurrence of specific time domain difference event-related potential components (like the DERP) in specific regions correlates with subject responsiveness to specific stimulus. According to various examples, ERP measures are enhanced using EEG time-frequency measures (ERPSP) in response to the presentation of the marketing and entertainment stimuli. Specific portions are extracted and isolated to identify ERP, DERP and ERPSP analyses to perform. In particular examples, an EEG frequency estimation of attention, emotion and memory retention (ERPSP) is used as a co-factor in enhancing the ERP, DERP and time-domain response analysis.

EOG measures saccades to determine the presence of attention to specific objects of stimulus. Eye tracking measures the subject's gaze path, location and dwell on specific objects of stimulus. According to various examples, EOG and eye tracking is enhanced by measuring the presence of lambda waves (a neurophysiological index of saccade effectiveness) in the ongoing EEG in the occipital and extra striate regions, triggered by the slope of saccade-onset to estimate the significance of the EOG and eye tracking measures. In particular examples, specific EEG signatures of activity such as slow potential shifts and measures of coherence in time-frequency responses at the Frontal Eye Field (FEF) regions that preceded saccade-onset are measured to enhance the effectiveness of the saccadic activity data.

GSR typically measures the change in general arousal in response to stimulus presented. According to various examples, GSR is enhanced by correlating EEG/ERP responses and the GSR measurement to get an enhanced estimate of subject engagement. The GSR latency baselines are used in constructing a time-corrected GSR response to the stimulus. The time-corrected GSR response is co-factored with the EEG measures to enhance GSR significance measures.

According to various examples, facial emotion encoding uses templates generated by measuring facial muscle positions and movements of individuals expressing various emotions prior to the testing session. These individual specific facial emotion encoding templates are matched with the individual responses to identify subject emotional response. In particular examples, these facial emotion encoding measurements are enhanced by evaluating inter-hemispherical asymmetries in EEG responses in specific frequency bands and measuring frequency band interactions. The techniques of the present disclosure recognize that not only are particular frequency bands significant in EEG responses, but particular frequency bands used for communication between particular areas of the brain are significant. Consequently, these EEG responses enhance the EMG, graphic and video based facial emotion identification.

According to various examples, post-stimulus versus pre-stimulus differential measurements of ERP time domain components in multiple regions of the brain (DERP) are measured at 607. The differential measures give a mechanism for eliciting responses attributable to the stimulus. For example the messaging response attributable to an ad or the brand response attributable to multiple brands is determined using pre-experience and post-experience estimates At 609, target versus distracter stimulus differential responses are determined for different regions of the brain (DERP). At 613, event related time-frequency analysis of the differential response (DERPSPs) are used to assess the attention, emotion and memory retention measures across multiple frequency bands. According to various examples, the multiple frequency bands include theta, alpha, beta, gamma and high gamma or kappa.

At 615, neuro-response lulls in source material are identified. For example, there may be locations in a particular media stream that elicit minimal neuro-response measurements. These lulls may last several seconds in duration in a commercial or may cover several feet of space on a supermarket shelf. These locations with insignificant neuro-response activity may be selected a potential locations where new stimulus material may be introduced. For example, brand images, messages, video clips, newly packaged products, etc. may all be part of the stimulus material selected for introduction into source material. Although lulls may be used to select candidate locations for the introduction of stimulus material, it should be noted that a variety of mechanisms may be used. In some examples, non-changing portions such as still screens in a video or blank or common colored areas in an image may be selected as candidate locations. Locations having little change in relation to neighboring locations may also be selected. In still other examples, locations are manually selected. At 623, multiple trials are performed with introduced stimulus material in different spatial and temporal locations to assess the impact of introduction at each of the different spatial and temporal locations.

For example, introduction of new products at location A on a billboard may lead to more significant neuro-response activity for the billboard in general. Introduction of an image onto a video stream may lead to greater emotional engagement and memory retention. In other examples, increased neuro-response activity for introduced material may detract from neuro-response activity for other portions of source material. For examples, a salient image on one part of a billboard may lead to reduced dwell times for other portions of a billboard. Acve, aggregated neuro-response measurements are identified to determine optimal locations for introduction of stimulus material.

At 625, processed data is provided to a data communication device for transmission over a network such as a wireless, wireline, satellite, or other type of communication network capable of transmitting data. Data is provided to response integration system at 627. According to various examples, the data communication device transmits data using protocols such as the File Transfer Protocol (FTP), Hypertext Transfer Protocol (HTTP) along with a variety of conventional, bus, wired network, wireless network, satellite, and proprietary communication protocols. The data transmitted can include the data in its entirety, excerpts of data, converted data, and/or elicited response measures. According to various examples, data is sent using a telecommunications, wireless, Internet, satellite, or any other communication mechanisms that is capable of conveying information from multiple subject locations for data integration and analysis. The mechanism may be integrated in a set top box, computer system, receiver, mobile device, etc.

In particular examples, the data communication device sends data to the response integration system 627. According to various examples, the response integration system 627 combines the analyzed responses to the experience/stimuli, with information on the available stimuli and its attributes. A variety of responses including user behavioral and survey responses are also collected an integrated. At 629, a location is selected for the introduction of stimulus material.

According to various examples, the response integration system combines analyzed and enhanced responses to the stimulus material while using information about stimulus material attributes such as the location, movement, acceleration, and spatial relationships of various entities and objects. In particular examples, the response integration system also collects and integrates user behavioral and survey responses with the analyzed and enhanced response data to more effectively assess stimulus location characteristics.

According to various examples, the stimulus location selection system provides data to a repository for the collection and storage of demographic, statistical and/or survey based responses to different entertainment, marketing, advertising and other audio/visual/tactile/olfactory material. If this information is stored externally, this system could include a mechanism for the push and/or pull integration of the data—including but not limited to querying, extracting, recording, modifying, and/or updating. This system integrates the requirements for the presented material, the assessed neuro-physiological and neuro-behavioral response measures, and the additional stimulus attributes such as demography/statistical/survey based responses into a synthesized measure for the selection of stimulus locations.

According to various examples, the repository stores information for temporal, spatial, activity, and event based components of stimulus material. For example, neuro-response data, statistical data, survey based response data, and demographic data may be aggregated and stored and associated with a particular component in a video stream.

Figure 7:
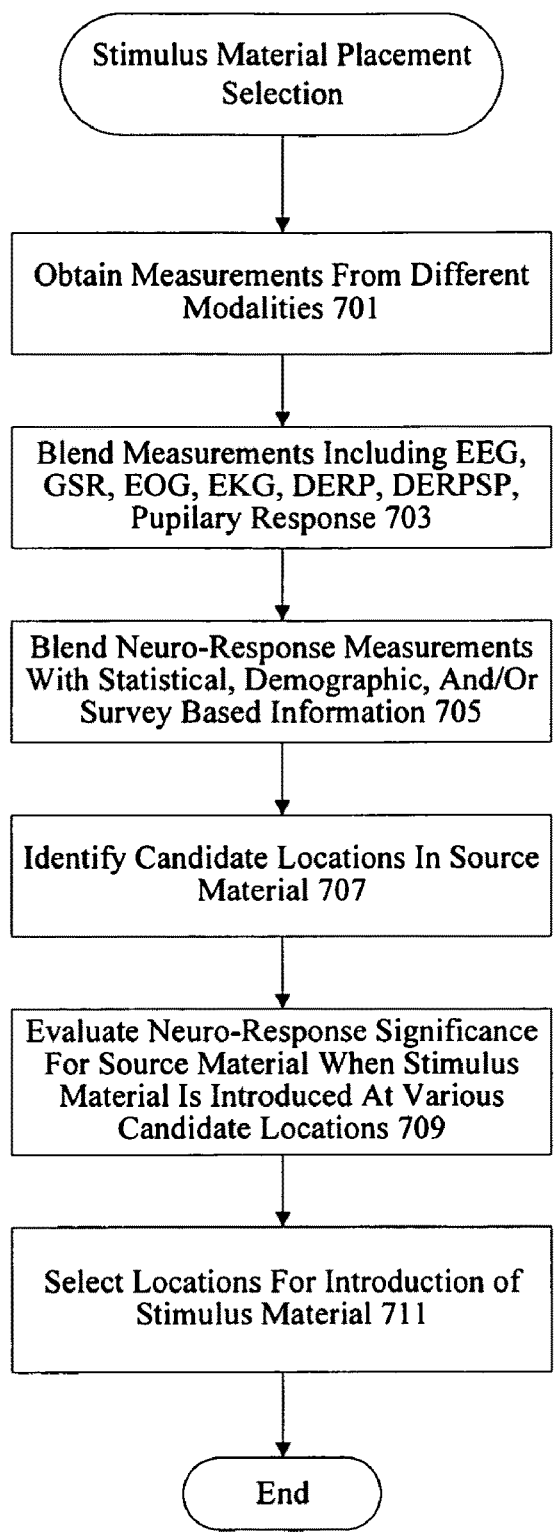
FIG. 7 illustrates one example of technique for analyzing temporal and spatial location selection data.

FIG. 7 illustrates an example of a technique for selecting stimulus locations experience. According to various examples, measurements from different modalities are obtained at 701. According to various examples, measurements including EEG, GSR, EOG, EKG, DERP, DERPSP, Pupilary Response, etc., are blended to obtain a combined measurement at 703. In particular examples, each measurement may have to be aligned appropriately in order to allow blending. According to various examples, a response integration system includes mechanisms to use and blend different measures from across the modalities from the data analyzer. In particular examples, the data includes the EEG, GSR, EOG, EKG, DERP, DERPSPs, pupilary response, GSR, eye movement, coherence, coupling and lambda wave based response. Measurements across modalities are blended to select one or more stimulus locations.

At 705, neuro-response measurements are combined with statistical, demographic, and/or survey based information. At 707, candidate locations for the introduction of stimulus material are identified. Candidate locations may include lulls, locations with less significant or insignificant neuro-response activity, non-changing scenes, or manually selected positions. In still other examples, candidate locations are identified by a stimulus material provider. A variety of mechanisms can be used to identify candidate locations. At 709, neuro-response significance is evaluated for the source material when stimulus material is introduced at the various candidate locations. Evaluation may include memory retention, emotional engagement, attention of source material are locations where stimulus material is introduced or in the aggregate. In some examples, differential measurements of ERP time domain components at multiple regions of the brain are determined (DERP). Event related time-frequency analysis of the differential response is performed to assess the attention, emotion and memory retention (DERPSPs) across multiple frequency bands including but not limited to theta, alpha, beta, gamma and high gamma. In particular examples, single trial and/or averaged DERP and/or DERPSPs can be used to further compare locations for the introduction of stimulus material.

At 711, preferred locations in the source material are selected for the introduction of stimulus material.

The location and placement assessment system can further include an adaptive learning component that refines profiles and tracks variations responses to particular stimuli or series of stimuli over time.

Figure 8:
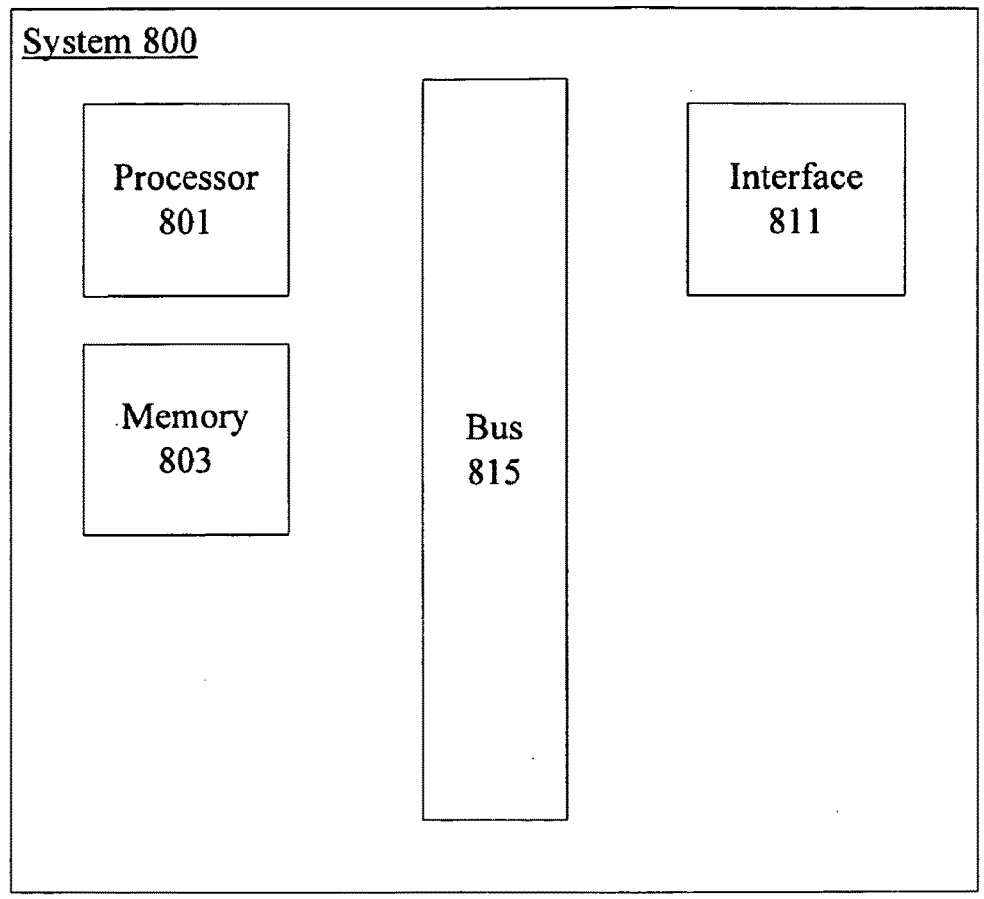
FIG. 8 provides one example of a system that can be used to implement one or more mechanisms.

According to various examples, various mechanisms such as the data collection mechanisms, the intra-modality synthesis mechanisms, cross-modality synthesis mechanisms, etc. are implemented on multiple devices. However, it is also possible that the various mechanisms be implemented in hardware, firmware, and/or software in a single system. FIG. 8 provides one example of a system that can be used to implement one or more mechanisms. For example, the system shown in FIG. 8 may be used to implement a stimulus location selection system.

According to particular examples, a system 800 suitable for implementing particular examples of the present disclosure includes a processor 801, a memory 803, an interface 811, and a bus 815 (e.g., a PCI bus). When acting under the control of appropriate software or firmware, the processor 801 is responsible for such tasks such as pattern generation. Various specially configured devices can also be used in place of a processor 801 or in addition to processor 801. The complete implementation can also be done in custom hardware. The interface 811 is typically configured to send and receive data packets or data segments over a network. Particular examples of interfaces the device supports include host bus adapter (HBA) interfaces, Ethernet interfaces, frame relay interfaces, cable interfaces, DSL interfaces, token ring interfaces, and the like.

In addition, various high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as data synthesis.

According to particular examples, the system 800 uses memory 803 to store data, algorithms and program instructions. The program instructions may control the operation of an operating system and/or one or more applications, for example. The memory or memories may also be configured to store received data and process received data.

Because such information and program instructions may be employed to implement the systems/methods described herein, the present disclosure relates to tangible, machine readable media that include program instructions, state information, etc. for performing various operations described herein. Examples of machine-readable media include, but are not limited to, magnetic media such as hard disks, floppy disks, and magnetic tape; optical media such as CD-ROM disks and DVDs; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Although the foregoing disclosure has been described in some detail for purposes of clarity of understanding, it will be apparent that certain changes and modifications may be practiced within the scope of the appended claims. Therefore, the present examples are to be considered as illustrative and not restrictive and the disclosure is not to be limited to the details given herein, but may be modified within the scope and equivalents of the appended claims.

What is claimed is:

1. A method comprising:

analyzing first neuro-response data from a first subject exposed to source material, the first neuro-response data comprising first electroencephalographic data from a first frequency band and second electroencephalographic data from a second frequency band, the second frequency band being different than the first frequency band, the first neuro-response data gathered from a frontal eye field (FEF) region of a brain of the first subject;

identifying, using a processor, a candidate location in the source material for introduction of an advertisement or entertainment based on an interaction between the first frequency band and the second frequency band, the interaction including a degree of coherence between a first change in amplitude of the first frequency band measured before saccade onset and a second change in amplitude of the second frequency band measured before saccade onset;

analyzing second neuro-response data from at least one of the first subject or a second subject exposed to a combination of the source material and the advertisement or entertainment inserted in the candidate location, the second neuro-response data gathered from the FEF region of at least one of the brain of the first subject or a brain of the second subject; and determining an effectiveness of the advertisement or entertainment based on the second neuro-response data.

2. A system comprising:

an analyzer to analyze first neuro-response data from a first subject exposed to source material, the first neuro-response data comprising first electroencephalographic data from a first frequency band and second electroencephalographic data from a second frequency band, the second frequency band being different than the first frequency band, the first neuro-response data gathered from a frontal eye field (FEF) region of a brain of the first subject; and a processor to identify a candidate location in the source material for introduction of an advertisement or entertainment based on a degree of coherence between a first change in amplitude of the first frequency band measured before saccade onset and a second change in amplitude of the second frequency band measured before saccade onset, the analyzer to analyze second neuro-response data from at least one of the first subject or a second subject exposed to a combination of the source material and the advertisement or entertainment inserted in the candidate location, the second neuro-response data gathered from the FEF region of at least one of the brain of the first subject or a brain of the second subject, and the processor to determine an effectiveness of the advertisement or entertainment based on the second neuro-response data.

3. A tangible machine readable storage device or storage disc comprising machine readable instructions which, when read, cause a machine to at least:

analyze first neuro-response data from a first subject exposed to source material, the first neuro-response data comprising a first frequency band of electroencephalographic data and a second frequency band of electroencephalographic data, the second frequency band being different than the first frequency band, the first neuro-response data gathered from a frontal eye field (FEF) region of a brain of the first subject;

identify a candidate location in the source material for introduction of an advertisement or entertainment based on a degree of coherence between a first change in amplitude of the first frequency band measured before saccade onset and a second change in amplitude of the second frequency band measured before saccade onset;

analyze second neuro-response data from at least one of the first subject or a second subject exposed to a combination of the source material and the advertisement or entertainment inserted in the candidate location, the second neuro-response data gathered from the FEF region of at least one of the brain of the first subject or a brain of the second subject; and determine an effectiveness of the advertisement or entertainment based on the second neuro-response data.

4. A system comprising:

an analyzer to:

analyze first neuro-response data from a first subject exposed to source material, the first neuro-response data comprising first electroencephalographic data from a first frequency band and second electroencephalographic data from a second frequency band, the second frequency band being different than the first frequency band, the first neuro-response data gathered from a frontal eye field (FEF) region of a brain of the first subject;

determine an interaction between the first frequency band and the second frequency band based on the analysis, the interaction including a degree of coherence between a first change in amplitude of the first frequency band measured before saccade onset and a second change in amplitude of the second frequency band measured before saccade onset; and
generate a response profile for the first subject based on the interaction; and
a processor to:
link the response profile with candidate location data for the source material; and
identify a candidate location in the source material for introduction of an advertisement or entertainment based on the response profile and the candidate location data,
the analyzer to analyze second neuro-response data from at least one of the first subject or a second subject exposed to a combination of the source material and the advertisement or entertainment inserted in the candidate location, the second neuro-response data gathered from the FEF region of at least one of the brain of the first subject or a brain of the second subject, and
the processor to determine an effectiveness of the advertisement or entertainment based on the second neuro-response data.

5. The system of claim 4, wherein the processor is to identify the candidate location based on a spatial characteristic of the source material.

6. The system of claim 4, wherein the processor is to identify a candidate location based on a temporal characteristic of the source material.

7. The system of claim 4, wherein the analyzer is to further generate the response profile based on survey response data collected from the first subject.

8. The system of claim 4, wherein the analyzer is to further generate the response profile based on third neuro-response data from the first subject, the third neuro-response data including at least one of pupillary response data, electrooculographic data, or galvanic skin response data.

9. The system of claim 4, wherein the processor is to:
identify a decrease in first activity in the first frequency band and the second frequency band at first time relative to second activity in the first frequency band and the second frequency band at a second time; and
identify the candidate location in the source material based on the first time.

10. The system of claim 4, wherein the candidate location is a first candidate location and the analyzer is to generate a second response profile for a third subject based on third neuro-response data from the third subject exposed to the source material, the processor to identify a second candidate location in the source material based on the second response profile, the first candidate location different from the second candidate location.

11. The system of claim 4, wherein the processor is to change the candidate location based on the first neuro-response data and third neuro-response data collected from the first subject at a time after the first neuro-response data.

12. A tangible machine readable storage device or storage disc comprising machine readable instructions which, when read, cause a machine to at least:
analyze first neuro-response data from a first subject exposed to source material, the first neuro-response data comprising first electroencephalographic data from a first frequency band and second electroencephalographic data from a second frequency band, the second frequency band being different than the first frequency band, the first neuro-response data gathered from a frontal eye field (FEF) region of a brain of the first subject;
determine an interaction between the first frequency band and the second frequency band based on the analysis, the interaction including a degree of coherence between a first change in amplitude of the first frequency band measured before saccade onset and a second change in amplitude of the second frequency band measured before saccade onset;
generate a response profile for the first subject based on the interaction;
link the response profile with candidate location data for the source material;
identify a candidate location in the source material for introduction of an advertisement or entertainment based on the response profile and the candidate location data;
analyze second neuro-response data from at least one of the first subject or a second subject exposed to a combination of the source material and the advertisement or entertainment inserted in the candidate location, the second neuro-response data gathered from the FEF region of at least one of the brain of the first subject or a brain of the second subject; and
determine an effectiveness of the advertisement or entertainment based on the second neuro-response data.

13. The tangible machine readable storage device or storage disc of claim 12, wherein the instructions, when executed, further cause the machine to identify the candidate location based on a spatial characteristic of the source material.

14. The tangible machine readable storage device or storage disc of claim 12, wherein the instructions, when executed, further cause the machine to the processor is to identify a candidate location based on a temporal characteristic of the source material.

15. The tangible machine readable storage device or storage disc of claim 12, wherein the instructions, when executed, further cause the machine to generate the response profile based on survey response data collected from the first subject.

16. The tangible machine readable storage device or storage disc of claim 12, wherein the instructions, when executed, further cause the machine to generate the response profile based on third neuro-response data from the first subject, the third neuro-response data including at least one of pupillary response data, electrooculographic data, or galvanic skin response data.

17. The tangible machine readable storage device or storage disc of claim 12, wherein the instructions, when executed, further cause the machine to:
identify a decrease in first activity in the first frequency band and the second frequency band at first time relative to second activity in the first frequency band and the second frequency band at a second time; and
identify the candidate location in the source material based on the first time.

18. The tangible machine readable storage device or storage disc of claim 12, wherein the candidate location is a first candidate location and wherein the instructions, when executed, further cause the machine to:
generate a second response profile for a third subject based on third neuro-response data from the third subject exposed to the source material; and
identify a second candidate location in the source material based on the second response profile, the first candidate location different from the second candidate location.

19. The tangible machine readable storage device or storage disc of claim 12, wherein the instructions, when executed, further cause the machine to change the candidate location based on the first neuro-response data and third neuro-response data collected from the first subject at a time after the first neuro-response data.

* * * * *